US007557251B2

(12) United States Patent
Wang et al.

(10) Patent No.: US 7,557,251 B2
(45) Date of Patent: Jul. 7, 2009

(54) PRODUCTION OF GOSSYPOL CO-CRYSTALS

(75) Inventors: Shaomeng Wang, Saline, MI (US); Jianyong Chen, Ann Arbor, MI (US); John F. W. Keana, Eugene, OR (US); Ming Guo, San Diego, CA (US)

(73) Assignee: The Regents of the University of Michigan, Ann Arbor, MI (US)

( * ) Notice: Subject to any disclaimer, the term of this patent is extended or adjusted under 35 U.S.C. 154(b) by 125 days.

(21) Appl. No.: 11/729,638

(22) Filed: Mar. 29, 2007

(65) Prior Publication Data

US 2008/0021110 A1 Jan. 24, 2008

Related U.S. Application Data

(60) Provisional application No. 60/788,025, filed on Mar. 30, 2006.

(51) Int. Cl.
| C07C 39/12 | (2006.01) |
| C07C 39/38 | (2006.01) |
| C07C 39/10 | (2006.01) |
| C07C 53/08 | (2006.01) |

(52) U.S. Cl. .................. 568/732; 568/737; 568/763; 562/607

(58) Field of Classification Search .................. None
See application file for complete search history.

(56) References Cited

U.S. PATENT DOCUMENTS

| 2003/0008924 A1 | 1/2003 | Wang |
| 2004/0214902 A1 | 10/2004 | Wang |

FOREIGN PATENT DOCUMENTS

| CN | 1033795 | 7/1989 |
| CN | 1557799 | * 12/2004 |

OTHER PUBLICATIONS

Adams, Jerry M., et al., "The Bcl-2 Protein Family: Arbiters of Cell Survival,", Science, Aug. 28, 1998, vol. 281, pp. 1322-1326.
Amberger, Verena R., et al., "Spreading and Migration of Human Glioma and Rat C6 Cells on Central Nervous System Myelin in Vitro is Correlated with Tumor Malignancy and Involves a Metalloproteolytic Activity," Cancer Research, 58, Jan. 1, 1998, pp. 149-158.
Bushunow, Peter, et al., "Gossypol treatment of recurrent adult malignant gliomas," Journal of Neuro-Oncology 43: pp. 79-86 (1999).
Cass, Quezia B., et al., "Determination of Gossypol Enantiomer Ratio in Cotton Plants by Chiral Higher-Performance Liquid Chromatography," Journal of Agricultural and Food Chemistry (2004), 52, pp. 5822-5827.
Ciesielska, Barbara, et al., "Emission properties of gossypol in solution" Chemical Physics Letters 353 (2002), pp. 69-76.
Del Bufalo, Donatella, "Bcl-2 overexpression enhances the metastatic potential of a human breast cancer line," The FASEB Journal, Oct. 1997, vol. 11, No. 12, pp. 947-953.
Deveraux, Quinn L., et al., "IAP family proteins—suppressors of apoptosis", Genes & Development 13:239-252 (1999).
Dowd, Michael K., "Crystal and Molecular Structure of an Enantiomeric Gossypol-Acetic Acid Clathrate", Journal of the American Oil Chemists' Society (JAOCS), vol. 76(11) pp. 1259-1392 (1999), pp. 1343-1350.
Dowd, Michael K., "Preparation of Enantiomeric Gossypol by Crystallization," Chirality 15:486-493 (2003).
Fernandez, Y., et al., "Bcl-xL promotes metastatis of breast cancer cells by induction of cytokines resistance," Cell Death and Differentiation (2000) 7, pp. 350-359.
Flack, Mary R., "Oral Gossypol in the Treatment of metastatic Adrenal Cancer," Journal of Clinical Endocrinology and Metabolism, vol. 76, No. 4, Jan./Jun. 1993, pp. 1019-1024.
Freedman, Teresa B., et al., "Determination of the Absolute Configuration and Solution Conformation of Gossypol by Vibrational Circular Dichroism," Chirality 15:196-200 (2003).
Frisch, Steven M., et al., "Integrins and anoikis," Current Opinion in Cell Biology, vol. 9, No. 5, Oct. 1997, pp. 701-706.
Gdaniec, Maria, et al., "Comprehensive Supramolecular Chemistry, 5: Gossypol," vol. 6, (1996), pp. 117-145.
Hua, Zhou Rui, "Isolation of (-) Gossypol from natural Plant," Contraception, Mar. 1988, vol. 37, No. 3, pp. 239-245.
Matlin, S.A., et al., "Large-Scale Resolution of Gossypol Enantiomers for Biological Evaluation," Contraception, vol. 37, No. 3, Mar. 1988, pp. 229-237.
Pedersen, Paal-Henning, et al., "Migratory Pattern of Fetal Rat Brain Cells and Human Glioma Cells in the Adult Rat Brain," Cancer Research, 53, Nov. 1, 1993, pp. 5159-5165.
Reed, John C., "BCL-2 Family Proteins: Regulators of Cell Death Involved in the Pathogenesis of Cancer and Resistance to Therapy," Journal of Cellular Biochemistry 60:23-32 (1996).
Reed, John C., "Bcl-2 Family Proteins: Strategies for Overcoming Chemoresistance in Cancer," Advances in Pharmacology, vol. 41, (1997), pp. 501-532.
Reed, John C., "Double identity for proteins of the Bcl-2 family," Nature, vol. 387, Jun. 19, 1987, pp. 773-776.
Rubio, Nuria, et al., "Metastatic Behavior of Human Breast Carcinomas Overexpressing the Bcl-xL Gene: A Role in Dormancy and Organospecificity," Laboratory Investigation, vol. 81, No. 5, May 2001, pp. 725-734.

(Continued)

*Primary Examiner*—Karl J Puttlitz
(74) *Attorney, Agent, or Firm*—Casimir Jones S.C.

(57) ABSTRACT

This invention relates to relates to methods for producing gossypol acetic acid co-crystals and (−)-gossypol acetic acid co-crystals. The invention also relates to pharmaceutical compositions comprising gossypol acetic acid co-crystals and (−)-gossypol acetic acid co-crystals and the use of gossypol acetic acid co-crystals and (−)-gossypol acetic acid co-crystals for inducing apoptosis in cells and for sensitizing cells to the induction of apoptotic cell death.

2 Claims, No Drawings

OTHER PUBLICATIONS

Salvesen, Guy S., et al., "IAP Proteins: Blocking the Road to Death's Door," Nature Review: Molecular Cell Biology, vol. 3, Jun. 2002, pp. 401-410.

Sampath, D.S., et al., "A Rapid Procedure for the Resolution of Racemic Gossypol," Journal of Chemical Society (1996), pp. 649-650.

Stipanovic, Robert D., "Occurrence of (+) and (-) Gossypol in Wild Species of cotton and in Gossyplum hirsutum Var. marie-galante (Watt) Hutchinson," Journal of Agricultural and Food Chemistry (2005), 53, pp. 6266-6271.

Stipanovic, Robert, et al., "Occurrence of (+) and (-) Gossypol in Seed from Wild Species of Gossypium," 2005 Beltwide Cotton Conferences, new Orleans, Louisiana, Jan. 4-7, 2005; file://E:\cotton05\index.html printed Mar. 13, 2008.

Van Poznak, Catherine, et al., "Oral gossypol in the treatment of patients with refractory metastatic breast cancer: A phase I/II clinical trial," Breast Cancer Research and Treatment 66: 239-249 (2001).

Wick, Wolfgang, et al., "BCL-2 promotes migration and invasiveness of human glioma cells", FEBS Letters 400 (1998), pp. 419-424.

Wu, Diafang, "An Overview of the Clinical Pharmacology and Therapeutic potential of Gossypol las Male Contraceptive Agent and in Gynaecological Disease," Drugs, 38 (3): (1989), pp. 333-341.

Yikang, Si., et al., "Studies on Resolution of Racemic Gossypol, Separation of Hexaacetates of S-1-methylphen-ethylamino derivative of (+/-) gossypol)", Scientia Sinica (Series B)), vol. XXX, No. 3, Mar. 1987.

International Search Report and Written Opinion, PCT/US07/07604, dated Jul. 21, 2008.

CN1887838, Shanghai Institute of Organic Chemistry, Jan. 3, 2007, STN online citation 146:169229, Columbus, OH, USA, abstract.

CN1557799, Shanxi Rdragon Pharmaceutical Group Co.), Dec. 29, 2004, STN online citation 143:216598, Columbus, OH, USA, abstract.

Dowd, Chirality, 2003, 15(6), 486-493, STN online citation 14:164037, Columbus, OH, USA, abstract.

Dowd, Journal of the American Oil Chemist's Society (1999), 76(11), 13-43-1350, STN online citation 132-93495, Columbus, OH, USA, abstract.

* cited by examiner

US 7,557,251 B2

PRODUCTION OF GOSSYPOL CO-CRYSTALS

The present application claim priority to U.S. Provisional Application Ser. No. 60/788,025, filed Mar. 30, 2006, the entire disclosure of which is herein incorporated by reference in its entirety.

BACKGROUND OF THE INVENTION

1. Field of the Invention

This invention is in the field of medicinal chemistry. In particular, the invention relates to methods for producing gossypol acetic acid co-crystals and (−)-gossypol acetic acid co-crystals. The invention also relates to pharmaceutical compositions comprising gossypol acetic acid co-crystals or (−)-gossypol acetic acid co-crystals and the use of gossypol acetic acid co-crystals and (−)-gossypol acetic acid co-crystals for inducing apoptosis in cells and for sensitizing cells to the induction of apoptotic cell death.

2. Related Art

The aggressive cancer cell phenotype is the result of a variety of genetic and epigenetic alterations leading to deregulation of intracellular signaling pathways (Ponder, *Nature* 411:336 (2001)). The commonality for all cancer cells, however, is their failure to execute an apoptotic program, and lack of appropriate apoptosis due to defects in the normal apoptosis machinery is a hallmark of cancer (Lowe et al., *Carcinogenesis* 21:485 (2000)). Most of the current cancer therapies, including chemotherapeutic agents, radiation, and immunotherapy, work by indirectly inducing apoptosis in cancer cells. The inability of cancer cells to execute an apoptotic program due to defects in the normal apoptotic machinery is thus often associated with an increase in resistance to chemotherapy, radiation, or immunotherapy-induced apoptosis. Primary or acquired resistance of human cancer of different origins to current treatment protocols due to apoptosis defects is a major problem in current cancer therapy (Lowe et al., *Carcinogenesis* 21:485 (2000); Nicholson, *Nature* 407:810 (2000)). Accordingly, current and future efforts towards designing and developing new molecular target-specific anticancer therapies to improve survival and quality of life of cancer patients must include strategies that specifically target cancer cell resistance to apoptosis. In this regard, targeting crucial negative regulators that play a central role in directly inhibiting apoptosis in cancer cells represents a highly promising therapeutic strategy for new anticancer drug design.

Two classes of central negative regulators of apoptosis have been identified. The first class of regulators is the inhibitor of apoptosis proteins (IAPs) (Deveraux et al., *Genes Dev.* 13:239 (1999); Salvesen et al., *Nat. Rev. Mol. Cell. Biol.* 3:401 (2002)). IAPs potently suppress apoptosis induced by a large variety of apoptotic stimuli, including chemotherapeutic agents, radiation, and immunotherapy in cancer cells.

The second class of central negative regulators of apoptosis is the Bcl-2 family of proteins (Adams et al., *Science* 281:1322 (1998); Reed, *Adv. Pharmacol.* 41:501 (1997); Reed et al., *J. Cell. Biochem.* 60:23 (1996)). Bcl-2 is the founding member of the family and was first isolated as the product of an oncogene. The Bcl-2 family now includes both anti-apoptotic molecules such as Bcl-2 and Bcl-xL and pro-apoptotic molecules such as Bax, Bak, Bid, and Bad. Bcl-2 and Bcl-xL are overexpressed in many types of human cancer (e.g., breast, prostate, colorectal, lung), including Non-Hodgkin's lymphoma, which is caused by a chromosomal translocation (t14, 18) that leads to overexpression of Bcl-2. This suggests that many cancer cell types depend on the elevated levels of Bcl-2 and/or Bcl-xL to survive the other cellular derangements that simultaneously both define them as cancerous or pre-cancerous cells and cause them to attempt to execute the apoptosis pathway. Also, increased expression of Bcl-2 family proteins has been recognized as a basis for the development of resistance to cancer therapeutic drugs and radiation that act in various ways to induce cell death in tumor cells.

Bcl-2 and Bcl-xL are thought to play a role in tumor cell migration and invasion, and therefore, metastasis. Amberger et al., *Cancer Res.* 58:149 (1998); Wick et al., *FEBS Lett,* 440:419 (1998); Mohanam et al., *Cancer Res.* 53:4143 (1993); Pedersen et al., *Cancer Res.,* 53:5158 (1993). Bcl-2 family proteins appear to provide tumor cells with a mechanism for surviving in new and non-permissive environments (e.g., metastatic sites), and contribute to the organospecific pattern of clinical metastatic cancer spread. Rubio, *Lab Invest.* 81:725 (2001); Fernandez et al., *Cell Death Differ.* 7:350 (2000)). Anti-apoptotic proteins such as Bcl-2 and/or Bcl-xL are also thought to regulate cell-cell interactions, for example through regulation of cell surface integrins. Reed, *Nature* 387:773 (1997); Frisch et al., *Curr. Opin. Cell Biol.* 9:701 (1997); Del Bufalo et al., *FASEB J.* 11:947 (1997).

Therapeutic strategies for targeting Bcl-2 and Bcl-xL in cancer to restore cancer cell sensitivity and overcome resistance of cancer cells to apoptosis have been extensively reviewed (Adams et al., *Science* 281:1322 (1998); Reed, *Adv. Pharmacol.* 41:501 (1997); Reed et al., *J. Cell. Biochem.* 60:23 (1996)). Currently, Bcl-2 antisense therapy is in several Phase III clinical trials for the treatment of solid and non-solid tumors.

Gossypol is a naturally occurring double biphenolic compound derived from crude cotton seed oil (*Gossypium* sp.). Human trials of gossypol as a male contraceptive have demonstrated the safety of long term administration of these compounds (Wu, *Drugs* 38:333 (1989)). Gossypol has more recently been shown to have some anti-proliferative effects (Flack et al., *J. Clin. Endocrinol. Metab.* 76:1019 (1993); Bushunow et al., *J. Neuro-Oncol.* 43:79, (1999); Van Poznak et al., *Breast Cancer Res. Treat.* 66:239 (2001)). (−)-Gossypol and its derivatives recently have been shown to be potent inhibitors of Bcl-2 and Bcl-xL and to have strong anti-cancer activity (U.S. Patent Application Nos. 2003/0008924; 2004/0214902).

Several methods have been used to separate the (−)- and (+)-enantiomers of gossypol from enantiomeric mixtures. Derivatization of gossypol with optically active amines (e.g., S-1-methylphenethylamine, L-phenylalaminol, (+)-phenylalanine methyl ester) followed by separation of the diastereomers and hydrolysis of the derivatives has been reported. Yikang et al., *Scientia Sinica* 30:297 (1987); Sampath et al., *J. Chem. Soc., Chem. Commun.* 9:649 (1986); Matlin et al., *Contraception* 37:229 (1988). Chinese Patent No. 1017705B discloses the derivatization of gossypol using optically active primary amines, followed by separation of the enantiomers by chromatography or crystallization.

Gossypol is capable of forming a composition, e.g., a co-crystal or solvate, with many different solvent molecules in varying ratios. Typical compositions are those comprising gossypol with acetone or acetic acid. Compositions comprising gossypol and acetic acid are known in the art and commercially available (e.g., Sigma-Aldrich Corp., St. Louis, Mo.). Previous attempts to crystallize (−)-gossypol have resulted in crystals that are too poor for X-ray analysis (Gdaniec et al., "Gossypol," in Comprehensive Supramolecular Chemistry (Atwood et al. eds.), Vol. 6, Pergamon) or in co-crystals of (−)-gossypol and acetone when using a solution of gossypol acetic acid in acetone (Dowd et al., *J. Am. Oil*

Chem. Soc. 76:1343 (1999)) or in co-crystals of (−)-gossypol and 2,4-pentanedione (Dowd et al., *J. Chem. Crystallogr.* 34:559 (2004)).

SUMMARY OF THE INVENTION

The present invention relates to methods of producing gossypol acetic acid co-crystals and (−)-gossypol acetic acid co-crystals. The invention further relates to compositions comprising gossypol acetic acid co-crystals or (−)-gossypol acetic acid co-crystals. These compositions are useful for inhibiting the activity of anti-apoptotic Bcl-2 family proteins, inducing apoptosis in cells, and increasing the sensitivity of cells to inducers of apoptosis.

It is generally accepted that the inability of cancer cells or their supporting cells to undergo apoptosis in response to genetic lesions or exposure to inducers of apoptosis (such as anticancer agents and radiation) is a major factor in the onset and progression of cancer. The induction of apoptosis in cancer cells or their supporting cells (e.g., neovascular cells in the tumor vasculature) is thought to be a universal mechanism of action for virtually all of the effective cancer therapeutic drugs or radiation therapies on the market or in practice today. One reason for the inability of a cell to undergo apoptosis is increased expression and accumulation of anti-apoptotic Bcl-2 family proteins.

The present invention contemplates that exposure of animals suffering from cancer to therapeutically effective amounts of gossypol acetic acid co-crystals or (−)-gossypol acetic acid co-crystals that inhibit the function(s) of anti-apoptotic Bcl-2 family proteins will kill cancer cells or supporting cells outright (those cells whose continued survival is dependent on the overactivity of Bcl-2 family proteins) and/or render such cells as a population more susceptible to the cell death-inducing activity of cancer therapeutic drugs or radiation therapies. The present invention contemplates that gossypol acetic acid co-crystals or (−)-gossypol acetic acid co-crystals will satisfy an unmet need for the treatment of multiple cancer types, either when administered as monotherapy to induce apoptosis in cancer cells dependent on anti-apoptotic Bcl-2 family proteins function, or when administered in a temporal relationship with other cell death-inducing cancer therapeutic drugs or radiation therapies so as to render a greater proportion of the cancer cells or supportive cells susceptible to executing the apoptosis program compared to the corresponding proportion of cells in an animal treated only with the cancer therapeutic drug or radiation therapy alone.

In certain embodiments of the invention, it is expected that combination treatment of animals with a therapeutically effective amount of a composition of the present invention and a course of an anticancer agent or radiation will produce a greater tumor response and clinical benefit in such animals compared to those treated with the composition or anticancer drugs/radiation alone. Put another way, because the compositions lower the apoptotic threshold of all cells that express anti-apoptotic Bcl-2 family proteins, the proportion of cells that successfully execute the apoptosis program in response to the apoptosis inducing activity of anticancer drugs/radiation will be increased. Alternatively, the compositions of the present invention are expected to allow administration of a lower, and therefore less toxic and more tolerable, dose of an anticancer agent and/or radiation to produce the same tumor response/clinical benefit as the conventional dose of the anticancer agent/radiation alone. Since the doses for all approved anticancer drugs and radiation treatments are known, the present invention contemplates combination therapies with various combinations of known drugs/treatments with the present compositions. Also, since the compositions of the present invention act at least in part by inhibiting anti-apoptotic Bcl-2 family proteins, the exposure of cancer cells and supporting cells to therapeutically effective amounts of the compositions can be temporally linked to coincide with the attempts of cells to execute the apoptosis program in response to the anticancer agent or radiation therapy. Thus, in some embodiments, administering the compositions of the present invention in connection with certain temporal relationships, will provide especially efficacious therapeutic practices.

Gossypol acetic acid co-crystals or (−)-gossypol acetic acid co-crystals are useful for the treatment, amelioration, or prevention of disorders responsive to induction of apoptotic cell death, e.g., disorders characterized by dysregulation of apoptosis, including hyperproliferative diseases such as cancer. In certain embodiments, gossypol acetic acid co-crystals or (−)-gossypol acetic acid co-crystals can be used to treat, ameliorate, or prevent cancer that is characterized by resistance to cancer therapies (e.g., those which are chemoresistant, radiation resistant, hormone resistant, and the like). In additional embodiments, gossypol acetic acid co-crystals or (−)-gossypol acetic acid co-crystals can be used to treat, ameliorate, or prevent metastatic cancer. In other embodiments, gossypol acetic acid co-crystals or (−)-gossypol acetic acid co-crystals can be used to treat hyperproliferative diseases characterized by overexpression of anti-apoptotic Bcl-2 family proteins.

The present invention provides methods of treating a viral, microbial, or parasitic infection in an animal, comprising administering to said animal a therapeutically effective amount of gossypol acetic acid co-crystals or (−)-gossypol acetic acid co-crystals.

The present invention provides methods of producing gossypol acetic acid co-crystals from gossypol acetic acid starting material comprising a mixture of (+)- and (−)-gossypol, the methods comprising recrystallizing gossypol acetic acid co-crystals from a recrystallization mixture of gossypol acetic acid starting material comprising a mixture of (+)- and (−)-gossypol in acetone and acetic acid.

The invention also provides gossypol acetic acid co-crystals produced by the methods of the invention.

The invention provides methods of producing (−)-gossypol acetic acid co-crystals from gossypol acetic acid starting material comprising a mixture of (+)- and (−)-gossypol, comprising:

(a) derivatizing gossypol acetic acid starting material comprising a mixture of (+)- and (−)-gossypol via imine (Schiff base) formation with an optically active amine to form gossypol imine diastereomers or a tautomer thereof;

(b) separating said diastereomers;

(c) hydrolyzing the imine diastereomer derived from (−)-gossypol to produce (−)-gossypol;

(d) separating said (−)-gossypol;

(e) forming (−)-gossypol acetone co-crystals; and (f) substituting the acetone in said (−)-gossypol acetone co-crystals with acetic acid to form (−)-gossypol acetic acid co-crystals.

The invention further provides methods of producing (−)-gossypol acetic acid co-crystals from (−)-gossypol acetone co-crystals, comprising substituting the acetone in said (−)-gossypol acetone co-crystals with acetic acid to form (−)-gossypol acetic acid co-crystals.

The invention also provides (−)-gossypol acetic acid co-crystals produced by the methods of the invention.

The invention also provides (−)-gossypol acetone co-crystals produced by the methods of the invention.

The invention further provides methods for reducing the level of impurities in gossypol acetic acid co-crystals or (−)-gossypol acetic acid co-crystals, comprising dissolving said co-crystals in acetone and removing the acetic acid.

The invention provides pharmaceutical compositions comprising gossypol acetic acid co-crystals or (−)-gossypol acetic acid co-crystals and a pharmaceutically acceptable carrier.

The invention further provides methods of making a pharmaceutical composition comprising admixing gossypol acetic acid co-crystals or (−)-gossypol acetic acid co-crystals in a therapeutically effective amount to induce apoptosis in cells or to sensitize cells to inducers of apoptosis with a pharmaceutically acceptable carrier The invention further provides kits comprising gossypol acetic acid co-crystals or (−)-gossypol acetic acid co-crystals and instructions for administering the composition to an animal. The kits may optionally contain other therapeutic agents, e.g., anticancer agents.

DETAILED DESCRIPTION OF THE INVENTION

The present invention relates to methods for producing gossypol acetic acid co-crystals and (−)-gossypol acetic acid co-crystals from gossypol acetic acid starting material comprising a mixture of (+)- and (−)-gossypol.

The term "gossypol acetic acid starting material comprising a mixture of (+)- and (−)-gossypol," as used herein, refers to a composition comprising a mixture of (+)- and (−)-gossypol, in any ratio, for which an increase in purity (e.g., chemical and/or chiral purity) is desired. The composition may be crystalline or non-crystalline. Gossypol acetic acid starting material comprising a mixture of (+)- and (−)-gossypol is typically not of high purity, e.g., containing at least 5% impurities, but includes gossypol acetic acid compositions of any purity, e.g., material that has already been purified at least once.

Gossypol acetic acid starting material comprising a mixture of (+)- and (−)-gossypol may be from any available source. One source is commercially available preparations. Gossypol acetic acid starting material comprising a mixture of (+)- and (−)-gossypol may also be obtained from cotton plants, e.g., from cottonseeds or other plant parts. Species of cotton vary widely both in the total content of gossypol and the optical activity of the gossypol. While many species of cotton contain gossypol that is around 50:50 (+) and (−), several species have been identified that contain either high levels of (+)-gossypol (e.g., *Gossypium hirsutum, G. arboreum, G. mustelinum, G. anomalum, G. gossypioides, G. capatis-viridis*, (up to about 97% (+)-gossypol)) or high levels of (−)-gossypol (e.g., *G. barbadense, G. darwinii, G. sturtianjm, G. areysianum, G. longicalyx, G. harknessii, G. costulatum* (up to about 65% (−)-gossypol)). See, e.g., Hua et al., *Contraception* 37:239 (1988); Cass et al., *J. Agric. Food Chem.* 52:5822 (2004); Stipanovic et al., *J. Agric. Food Chem.* 53:6266 (2005); Stipanovic et al., 2005 *Beltwide Cotton Conferences*, New Orleans, La., Jan. 4-7, 2005, p. 900. The enantiomeric ratio of gossypol also varies in different parts of the cotton plant. For example, in *G. barbadense* the seeds typically have an excess of (−)-gossypol, but the roots and flowers may contain an excess of (+)-gossypol (Cass et al., *J. Agric. Food Chem.* 52:5822 (2004)). Thus, a strain of cotton or a part thereof that is high in (−)-gossypol may be advantageously used as the source of the gossypol acetic acid starting material comprising a mixture of (+)- and (−)-gossypol for the present invention.

The term "gossypol acetic acid co-crystals," as used herein, refers to gossypol acetic acid co-crystals comprising a mixture of (+)- and (−)-gossypol in any ratio and acetic acid in a molar ratio of about 1:1 containing less than 5% impurities.

The term "racemic gossypol," as used herein, refers to gossypol compositions comprising about 50% (−)-enantiomer and about 50% (+)-enantiomer, and encompasses compositions comprising from about 45% to about 55% of each enantiomer.

The term "(−)-gossypol acetic acid co-crystals," as used herein, refers to (−)-gossypol acetic acid co-crystals comprising gossypol and acetic acid in a molar ratio of about 1:1 containing less than 5% impurities. (−)-Gossypol acetic acid co-crystals comprise an enantiomeric excess of (−)-gossypol. In one embodiment, (−)-gossypol acetic acid co-crystals comprise at least about 60%, 70%, 80%, 90%, 95%, 96%, 97%, 98%, 99%, 99.5%, or 99.9% (−)-gossypol. A preferred method to determine enantiomeric excess of (−)-gossypol us by chiral HPLC. In one example, the specific rotation ($[\alpha]_D$) of the (−)-gossypol in acetone at a concentration of 0.15 to 0.3 mg/mL at a temperature of 25° C. is about −300° to about −390°, about −375° to about −390°, or about −385° to about −390°. (See e.g., Dowd, *Chirality*, 15:486 (2003); Ciesielska et al., *Chem. Phys. Lett.* 353:69 (2992); Freedman et al., *Chirality*, 15:196 (2003); and Zhou et al., *Kexue Tongbao*, 28:1574 (1983)).

One aspect of the invention relates to methods of producing gossypol acetic acid co-crystals from gossypol acetic acid starting material comprising a mixture of (+)- and (−)-gossypol, the methods comprising recrystallizing gossypol acetic acid co-crystals from a solution of gossypol acetic acid crystals dissolved in a solvent. In one embodiment, the gossypol acetic acid co-crystals are recrystallized from a solution of gossypol acetic acid in a mixture of acetone and acetic acid. In a specific embodiment, gossypol acetic acid co-crystals are recrystallized from a recrystallization mixture comprising 6-10 mL of acetone and 1-5 mL of acetic acid per gram of gossypol acetic acid starting material comprising a mixture of (+)- and (−)-gossypol. In a preferred embodiment, gossypol acetic acid co-crystals are recrystallized from a recrystallization mixture comprising about 8 mL of acetone and about 3 mL of acetic acid per gram of gossypol acetic acid starting material comprising a mixture of (+)- and (−)-gossypol. The recrystallization mixture is held for about 15 minutes to about 100 minutes, e.g., about 30 minutes to about 60 minutes, to allow co-crystal formation. The recrystallization is carried out at ambient temperature, e.g., about 15° C. to about 30° C., e.g., about 22° C. Following the recrystallization, the crystals are harvested from the recrystallization mixture (e.g., by filtration) and washed with a non-polar solvent, e.g., pentane, hexene, hexane(s), heptane, or mixtures thereof. Preferably, the washing step is quick to avoid the incorporation of the non-polar solvent into the crystals. In a preferred embodiment, washing with heptane takes place for less than 2 minutes. It has been discovered that long washes with heptane give the heptane co-crystal. Thus, short washing times (less than 2 minutes) are preferred. The crystals may then be dried, e.g., in vacuo, while protected from light. The recrystallization may be repeated more than once (e.g., 2, 3, 4, 5, or more times) to improve the impurity profile, e.g., until gossypol co-crystals comprise less than about 5%, 4%, 3%, 2%, 1%, 0.5%, or 0.1% impurities. Once the desired impurity profile is obtained, a final recrystallization may be carried out at a lower temperature, e.g., about −20° C. to about 10° C., preferably about −10° C. to about 0° C. The recrystallization mixture is held for about 15 minutes to about 100 minutes, e.g., about 30 to about 60 minutes, and the resulting crystals are then filtered, washed and dried as described above.

In one embodiment, the gossypol acetic acid co-crystals have a purity of about 95%, 99%, or 99.5%.

In one embodiment, the method of producing gossypol acetic acid co-crystals produces a final product comprising less than about 5% total impurities, preferably less than about 3%, 2%, or 1%. In another embodiment, the final product comprises less than about 1% of any individual impurity other than hemi-anhydrogossypol, preferably less than about 0.25%. In another embodiment, the final product comprises less than 4% hemi-anhydrogossypol, preferably less than about 2%. In a further embodiment, the final product comprises less than about 4% acetone, preferably less than about 2%.

A second aspect of the invention relates to methods of producing (−)-gossypol acetic acid co-crystals from gossypol acetic acid starting material comprising a mixture of (+)- and (−)-gossypol. In one embodiment the gossypol acetic acid starting material comprising a mixture of (+)- and (−)-gossypol is gossypol acetic acid co-crystals. In a first step in the methods, gossypol acetic acid starting material comprising a mixture of (+)- and (−)-gossypol is derivatized via imine (Schiff base) formation with an optically active amine to form diastereomers. As used herein, the term "imine" includes other tautomers such as eneamine tautomers and stereoisomers thereof. The invention further encompasses alternative structures that may be formed from the derivatization of gossypol with an amine (e.g., an oxazolidine). In one embodiment, the optically active amine is L-phenylalanine methyl ester, S-1-methylphenethylamine, or L-phenylalaminol or the corresponding HCl salt. The derivatization may be carried out in the absence of oxygen, e.g., under a nitrogen purge. The derivatization is carried out in the presence of a nonpolar and/or polar solvent, e.g., dichloromethane and/or isopropanol, for a time period of about 0.5 to about 3 hours, e.g., about 1 hour to about 2 hours. A dehydrating agent such as sodium sulfate or a molecular sieve, e.g., type 3 Å, is then added, along with suitable reagents for buffering the reaction mix at a pH of about 5 to about 7, e.g., about 6. One suitable buffering agent is sodium bicarbonate. The reaction mixture is then stirred for at least about 15 minutes, e.g., at least about 30 minutes. The progression of the reaction may be monitored for completion. For example, the reaction mixture may be assayed for the absence of gossypol using thin layer chromatography (TLC) or preferably in real time by high pressure liquid chromatography (HPLC). If the reaction is incomplete, the pH may be adjusted back to about 6 by adding further buffering agents. The reaction is then continued for about 24 hours and again checked for completion of the reaction. After completion, the reaction mixture may be filtered to remove the solids and the solids washed with additional non-polar solvent, e.g., dichloromethane. The filtrates may then be evaporated to dryness, e.g., with a rotary evaporator with the bath set at about 30° C. to about 40° C.

The resultant diastereomers are then separated, e.g., by chromatography. In one embodiment, the diastereomers are separated by silica gel chromatography, e.g., Kromasil Si. The dried filtrate is reconstituted in a non-polar solvent, e.g., dichloromethane, and charged onto the column. The diastereomers are eluted with a solvent system comprising non-polar and polar solvents, e.g., 1:1 heptane:ethyl acetate. Column fractions may be monitored by HPLC and fractions containing the desired isomer (e.g., at least about 90%) may be pooled and evaporated. Impure fractions may be collected and passed over the column additional times. In one embodiment, the diastereomer mixture is held for less than 24 hours, preferably less than 12, 6, or 3 hours, prior to separation in order to avoid any increase in contamination with gossypol derivatives.

The separated R-(−)-gossypol bis-imine diastereomer may then be hydrolyzed to produce (−)-gossypol. The hydrolysis may be carried out in the absence of oxygen, e.g., under a nitrogen purge. The (−)-gossypol derivative is mixed with a polar solvent (e.g., tetrahydrofuran) and an acid (e.g., aqueous hydrochloric acid) and stirred for at least about 1 hour, e.g., at least about 5 hours. The extent of the reaction may be monitored by TLC or HPLC for depletion of both the bis- and mono-imine compounds to less than about 10%, preferably less than about 5%. If the reaction is not sufficient, it may be continued for at least about 15 hours and re-evaluated.

Once sufficient hydrolysis has occurred, the reaction mixture may then be washed with an aqueous brine solution. The aqueous brine solution may be back extracted with a polar solvent (e.g., ethyl acetate). The organic layers are then combined and washed with an alkaline aqueous solution (e.g., sodium bicarbonate) followed by a brine solution. The organic layers may then be evaporated to dryness, e.g., with a rotary evaporator with the bath set at about 30° C. to about 40° C.

The crude isolate is then dissolved in a solvent system comprising non-polar and polar solvents (e.g., 1:1 heptane:ethyl acetate) and passed over a silica gel plug using the same solvent system containing a small amount of acetic acid (to avoid sticking to the plug). Fractions may be collected and monitored for gossypol content using TLC or HPLC. Product-containing fractions may be pooled and evaporated to dryness, e.g., with a rotary evaporator with the bath set at about 30° C. to about 40° C.

If further purification of the (−)-gossypol is desired, the (−)-gossypol may be purified by chromatography over a hydrophilic resin, e.g., a dihydroxypropyl resin such as DIOL, e.g., YMC DIOL (120 angstrom×10-20 micron) (GL Sciences). The dried product from the previous step may be reconstituted in a solvent system comprising non-polar and polar solvents (e.g., 1:1 heptane:ethyl acetate) and purified over the column using the same solvent system. Fractions are collected, held at a reduced temperature (e.g., about 2° C. to about 8° C.), and the fractions assayed for gossypol content using TLC or HPLC. Fractions containing gossypol (e.g., at least 90%) may be pooled and evaporated to dryness, e.g., with a rotary evaporator with the bath set at about 30° C. to about 40° C. Fractions with less than 90% gossypol may be pooled and re-purified over the column.

As a final step, the purified (−)-gossypol may be dissolved in acetone (e.g., at about 4 mL per 1 g gossypol) and glacial acetic acid is added (about 1.5 mL per 1 g gossypol). The mixture may then be loaded into a suitable container for crystallization (e.g., a Büchi Ball). If there is no immediate crystallization, the solvent may be slowly removed by vacuum until a crystal mass appears. The mixture may then be held for about 15 minutes to about 100 minutes, e.g., about 30 minutes to about 60 minutes, and then filtered. The crystals may then be washed with the same ratio of acetone and acetic acid. Finally, the crystals may be soaked in acetic acid (about 3 mL per 1 g gossypol for about 20 to about 40 minutes, preferably about 30 minutes, and the acetic acid removed by filtration. The crystals may then be dried (e.g., in vacuo) for at least one hour, e.g., about 2 to about 4 hours. The crystals may be packaged and stored protected from light (e.g., in amber glass vials) at a reduced temperature (e.g., about −30° C. to about 0° C., preferably about −10° C. to about −20° C.

A further aspect of the invention relates to an alternative method of producing (−)-gossypol acetic acid co-crystals from gossypol acetic acid starting material comprising a mixture of (+)- and (−)-gossypol. In a first step in the methods, gossypol acetic acid starting material comprising a mixture of (+)- and (−)-gossypol is derivatized via imine (Schiff base) formation with an optically active amine (e.g., L-phenylalanine methyl ester hydrochloride) to form diastereomers. The derivatization may be carried out in the absence of oxygen, e.g., under a nitrogen purge. The derivatization is carried out in the presence of a mixture of a nonpolar solvent (e.g., dichloromethane) and water for a time period of about 5 to about 30 minutes, e.g., about 10 minutes to about 20 minutes with agitation. Suitable reagents are then added for buffering the reaction mix at a pH of about 5 to about 7, e.g., about 6. Suitable buffering agents include sodium bicarbonate and sodium sulfate. The reaction mixture is then agitated for a time period of about 5 to about 30 minutes, e.g., about 10 minutes to about 20 minutes, and then allowed to separate into two layers. The layers are separated and the aqueous layer washed twice with a nonpolar solvent (e.g., dichloromethane). The organic layers are combined, a drying agent (e.g., sodium sulfate) is added, the mixture is filtered and the filter cake washed with nonpolar solvent (e.g., dichloromethane). The organic filtrate is mixed with more drying agent and stirred for at least one hour, e.g., 2-4 hours and monitored for completion of the reaction using HPLC or TLC methods. After completion of the reaction, the reaction mixture is filtered and rinsed with a nonpolar solvent. The filtrate may then be evaporated to dryness, e.g., with a rotary evaporator with the bath set at about 30° C. to about 40° C. and the residue stored at reduced temperature, e.g., about −10 to about −20° C., until used for the next step.

The resultant diastereomers are then separated, e.g., by chromatography. In one embodiment, the diastereomers are separated by silica gel chromatography, e.g., a DAC column packed with PrincetonSPHER 10-20 mm/100 angstrom. The dried filtrate is reconstituted in a non-polar solvent, e.g., dichloromethane, and charged onto the column. The diastereomers are eluted with a solvent system comprising non-polar and polar solvents, e.g., 1:1 heptane:ethyl acetate. Column fractions may be monitored by HPLC and fractions containing the desired isomer (e.g., at least about 95%) may be pooled and evaporated. Impure fractions may be collected and passed over the column additional times. The pooled fractions may then be evaporated to dryness, e.g., with a rotary evaporator with the bath set at about 25° C. to about 35° C. and the residue stored at reduced temperature, e.g., about −10 to about −20° C. until used for the next step.

The separated R-(−)-gossypol bis-imine diastereomer may then be hydrolyzed to produce (−)-gossypol. The hydrolysis may be carried out in the absence of oxygen, e.g., under a nitrogen purge. The (−)-gossypol derivative is mixed with a polar solvent (e.g., tetrahydrofuran) and an acid (e.g., aqueous acetic acid and aqueous hydrochloric acid) and heated to about 35-45° C. for at least about 1 hour, e.g., about 2 hours to about 3 hours. The extent of the reaction may be monitored by TLC or HPLC for depletion of both the bis- and mono-imine compounds to less than about 10%, preferably less than about 5%.

Once sufficient hydrolysis has occurred, water is added and the mixture cooled to about 15 to about 20° C. overnight. The mixture is filtered and rinsed with water. The residue is mixed with aqueous acetic acid, e.g., 6:1 water:acetic acid for at least one hour, e.g., about 2 to about 3 hours, filtered, and the filter cake rinsed with water. The rinsed filter cake is then transferred to light-protected containers, e.g., amber glass bottles.

The crude isolate is then dissolved in acetone and crystallized for at least about 30 minutes, e.g., about one hour. The crystals are separated and rinsed with a mixture of heptane and acetone, e.g., 9:1 heptane:acetone, and then heptane. The crystals are dried, e.g., in a vacuum. The mother liquor also may be dried and recrystallized.

As a final step, the R-(−)-gossypol acetone co-crystals may be resuspended in acetic acid and held for at least about 5 minutes, e.g., about 10 to about 20 minutes and the crystals separated, e.g., by filtration, and rinsed with acetic acid. The co-crystals are then dried, e.g., and a vacuum, and stored in light-protected containers (e.g., in amber glass vials).

A further aspect of the invention relates to an alternative method of derivatizing gossypol acetic acid starting material comprising a mixture of (+)- and (−)-gossypol to form a Schiff base in the above-described methods of producing (−)-gossypol acetic acid co-crystals. A mixture of gossypol acetic acid starting material comprising a mixture of (+)- and (−)-gossypol and optically active amine (e.g., L-phenylalanine methyl ester hydrochloride) in a nonpolar solvent (e.g., dichloromethane) is treated with triethylamine and mixed for at least 2 hours, e.g., about 5 hours, optionally under an oxygen-free atmosphere. The reaction may be monitored for completion using HPLC or TLC methods. After completion of the reaction, the mixture is extracted with water and the organic phase separated and evaporated to dryness, e.g., with a rotary evaporator with the bath set at about 25° C. to about 35° C., followed by a high vacuum overnight.

In one embodiment, the (−)-gossypol acetic acid co-crystals have a purity of about 95%, 99%, or 99.5%.

In one embodiment, the method of producing (−)-gossypol acetic acid co-crystals produces a final product comprising less than about 5% total impurities, preferably less than about 3%. In another embodiment, the final product comprises less than about 1% of any individual impurity other than hemi-anhydrogossypol, preferably less than about 0.25%, even more preferably less than 0.1%. In another embodiment, the final product comprises less than about 4% hemi-anhydrogossypol, preferably less than about 2%. In another embodiment, the final product comprises less than about 4% water, preferably less than about 2%. In another embodiment, the final product comprises less than about 50 ppm heavy metals, preferably less than about 20 ppm. In another embodiment, the final product comprises less than about 10,000 ppm each of acetone, ethyl acetate, heptane, or hexane, preferably less than about 5,000 ppm. In another embodiment, the final product comprises less than about 10% (+)-gossypol, preferably less than about 5%.

In one aspect of the invention, a method to reduce the level of impurities during a process of manufacturing gossypol acetic acid co-crystals or (−)-gossypol acetic acid co-crystals is provided. In this method gossypol acetic acid co-crystals are converted to gossypol acetone co-crystals by dissolving the co-crystals in acetone and removing the acetic acid. The removal of the acetic acid results in a significant decrease in the level of impurities. The gossypol acetone co-crystals are then converted to gossypol acetic acid co-crystals as described above for the last step of purification. In one embodiment, the method of reducing impurities may be used for gossypol acetic co-crystals that are impure or for gossypol acetic acid co-crystals which were originally of high purity but in which impurities have developed over time. Additionally, the method may be applied to the mother liquor from the crystallization of gossypol acetic acid co-crystals.

In one aspect of the invention, the manufacturing process for gossypol acetic acid co-crystals and (−)-gossypol acetic acid co-crystals may be monitored for the presence of impurities. The monitoring may take place before the manufacturing process has been started (i.e., testing the starting material), during one or more steps of the manufacturing process, and/or after the final product is manufactured. Examples of impurities that may be detected and monitored include, but are not limited to, anhydrogossypol, hemi-anhydrogossypol, gossypol monoacetate, dehydrogossypol, gossypol acetone acetal, mono-phenylalanine methyl ester imine of gossypol, gossypol dimer, hemigossypolone, gossypolone, hemigossypolonic acid, and gossypolonic acid. The presence of (+)-gossypol acetic acid may also be monitored during the manufacture of (−)-gossypol acetic acid co-crystals. The monitoring may occur by any method suitable for separating and identifying impurities, e.g., HPLC, TLC, and mass spectrometry.

It is known in the art and has been confirmed during the development of the present invention that the compound hemi-anhydrogossypol is in reversible equilibrium with gossypol. See, e.g., Berardi et al., *J. Am. Oil Chemists Soc.* 38:51 (1961). Gossypol acetic acid co-crystal and (−)-gossypol acetic acid co-crystal preparations contain measurable levels of hemi-anhydrogossypol. The level of hemi-anhydrogossypol increases upon storage of the co-crystals up to a point at which equilibrium is reached between the gossypol and the hemi-anhydrogossypol. Attempts to recover hemi-anhydrogossypol from the co-crystal product or from intermediate preparations results in the conversion of the hemi-anhydrogossypol back to the original gossypol species. Thus, the presence of hemi-anhydrogossypol in the gossypol acetic acid co-crystal as an alternative form of gossypol, at a level of less than about 4%, preferably less than about 2%, is contemplated as part of the present invention.

It has been found that gossypol acetic acid starting material comprising a mixture of (+)- and (−)-gossypol is sometimes contaminated with a significant amount of mono-aniline Schiff base of gossypol. This contamination is due to a method which is sometimes used for isolation of gossypol from cotton seeds which involves derivatization of the gossypol as the bis-aniline Schiff base. It has further been found that the mono-aniline Schiff base is difficult to remove during the production methods of the present invention. Thus, in one aspect of the invention, gossypol acetic acid starting material comprising a mixture of (+)- and (−)-gossypol is monitored for the presence of the mono-aniline Schiff base of gossypol and preparations of gossypol having low amounts of the contaminant are selected for use. In one embodiment, the amount of mono-aniline Schiff base of gossypol in gossypol acetic acid starting material comprising a mixture of (+)- and (−)-gossypol is less than about 5%, preferably less than about 4%, 3%, 2%, 1%, or is undetectable.

The invention further provides methods of producing (−)-gossypol acetone co-crystals from gossypol acetic acid starting material comprising a mixture of (+)- and (−)-gossypol, comprising:

(a) derivatizing gossypol acetic acid starting material comprising a mixture of (+)- and (−)-gossypol via imine (Schiff base) formation with an optically active amine to form gossypol imine diastereomers or a tautomer thereof;

(b) separating said diastereomers;

(c) hydrolyzing the imine diastereomer derived from (−)-gossypol to produce (−)-gossypol;

(d) separating said (−)-gossypol; and (e) forming (−)-gossypol acetone co-crystals.

Another aspect of the invention relates to (−)-gossypol acetone co-crystals. The term "(−)-gossypol acetone co-crystals" refers to co-crystals comprising (−)-gossypol and acetone in a molar ratio of about 1:3 to about 3:1, e.g., about 1:1. In one embodiment, the (−)-gossypol acetone co-crystals have a purity of about 95%, 99%, or 99.5%.

In certain embodiments, the (−)-gossypol acetone co-crystals produced by the methods of the invention contain less than 5% impurities, e.g., less than 3% impurities. In another embodiment, the (−)-gossypol acetone co-crystals comprise less than about 1% of any individual impurity other than hemi-anhydrogossypol, preferably less than about 0.25%, even more preferably less than 0.1%. In another embodiment, the (−)-gossypol acetone co-crystals comprise less than about 4% hemi-anhydrogossypol, preferably less than about 2%. In another embodiment, the (−)-gossypol acetone co-crystals comprise less than about 4% water, preferably less than about 2%. In another embodiment, the (−)-gossypol acetone co-crystals comprise less than about 50 ppm heavy metals, preferably less than about 20 ppm. In another embodiment, the (−)-gossypol acetone co-crystals comprise less than about 10,000 ppm each of ethyl acetate, heptane, or hexane, preferably less than about 5,000 ppm. In another embodiment, the (−)-gossypol acetone co-crystals comprise less than about 10% (+)-gossypol, preferably less than about 5%.

The present invention relates to compositions comprising gossypol acetic acid co-crystals or (−)-gossypol acetic acid co-crystals, which are useful as inhibitors of anti-apoptotic Bcl-2 family proteins. By inhibiting anti-apoptotic Bcl-2 family proteins, the gossypol sensitizes cells to inducers of apoptosis and, in some instances, itself induces apoptosis. Therefore, one aspect of the invention relates to methods of sensitizing cells to inducers of apoptosis and to methods of inducing apoptosis in cells, comprising administering gossypol acetic acid co-crystals or (−)-gossypol acetic acid co-crystals alone or in combination with an inducer of apoptosis. The invention further relates to methods of treating, ameliorating, or preventing disorders in an animal that are responsive to induction of apoptosis comprising administering to the animal gossypol acetic acid co-crystals or (−)-gossypol acetic acid co-crystals alone or in combination with an inducer of apoptosis. Such disorders include those characterized by a dysregulation of apoptosis and those characterized by overexpression of anti-apoptotic Bcl-2 family proteins.

The term "Bcl-2 family proteins," as used herein, refers to both the anti-apoptotic members of the Bcl-2 family, including, but not limited to, Bcl-2, Bcl-xL, Mcl-1, A1/BFL-1, BOO-DIVA, Bcl-w, Bcl-6, Bcl-8, and Bcl-y, and the pro-apoptotic members of the Bcl-2 family, including, but not limited to, Bak, Bax, Bad, tBid, Hrk, Bim, Bmf, as well as other Bcl-2 homology domain 3 (BH3) containing proteins that are regulated by gossypol compounds.

The term "overexpression of anti-apoptotic Bcl-2 family proteins," as used herein, refers to an elevated level (e.g., aberrant level) of mRNAs encoding for an anti-apoptotic Bcl-2 family protein(s), and/or to elevated levels of anti-apoptotic Bcl-2 family protein(s) in cells as compared to similar corresponding non-pathological cells expressing basal levels of mRNAs encoding anti-apoptotic Bcl-2 family proteins or having basal levels of anti-apoptotic Bcl-2 family proteins. Methods for detecting the levels of mRNAs encoding anti-apoptotic Bcl-2 family proteins or levels of anti-apoptotic Bcl-2 family proteins in a cell include, but are not limited to, Western blotting using anti-apoptotic Bcl-2 family protein antibodies, immunohistochemical methods, and methods of nucleic acid amplification or direct RNA detection. As important as the absolute level of anti-apoptotic Bcl-2 family proteins in cells is to determining that they overexpress anti-apoptotic Bcl-2 family proteins, so also is the relative level of anti-apoptotic Bcl-2 family proteins to other pro-apoptotic signaling molecules (e.g., pro-apoptotic Bcl-2 family proteins) within such cells. When the balance of these two are such that, were it not for the levels of the anti-apoptotic Bcl-2 family proteins, the pro-apoptotic signaling molecules would be sufficient to cause the cells to execute the apoptosis program and die, said cells would be dependent on the anti-apoptotic Bcl-2 family proteins for their survival. In such cells, exposure to an inhibiting effective amount of an anti-apoptotic Bcl-2 family protein inhibitor will be sufficient to cause the cells to execute the apoptosis program and die. Thus, the term "overexpression of an anti-apoptotic Bcl-2 family protein" also refers to cells that, due to the relative levels of pro-apoptotic signals and anti-apoptotic signals, undergo apoptosis in response to inhibiting effective amounts of compounds that inhibit the function of anti-apoptotic Bcl-2 family proteins.

The terms "anticancer agent" and "anticancer drug," as used herein, refer to any therapeutic agent (e.g., chemotherapeutic compounds and/or molecular therapeutic compounds), radiation therapies, or surgical interventions, used in the treatment of hyperproliferative diseases such as cancer (e.g., in mammals).

The term "therapeutically effective amount," as used herein, refers to that amount of the therapeutic agent sufficient to result in amelioration of one or more symptoms of a disorder, or prevent advancement of a disorder, or cause regression of the disorder. For example, with respect to the treatment of cancer, a therapeutically effective amount preferably refers to the amount of a therapeutic agent that decreases the rate of tumor growth, decreases tumor mass, decreases the number of metastases, increases time to tumor progression, or increases survival time by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%.

The terms "sensitize" and "sensitizing," as used herein, refer to making, through the administration of a first agent (e.g., gossypol or (−)-gossypol), an animal or a cell within an animal more susceptible, or more responsive, to the biological effects (e.g., promotion or retardation of an aspect of cellular function including, but not limited to, cell growth, proliferation, invasion, angiogenesis, or apoptosis) of a second agent. The sensitizing effect of a first agent on a target cell can be measured as the difference in the intended biological effect (e.g., promotion or retardation of an aspect of cellular function including, but not limited to, cell growth, proliferation, invasion, angiogenesis, or apoptosis) observed upon the administration of a second agent with and without administration of the first agent. The response of the sensitized cell can be increased by at least 10%, at least 20%, at least 30%, at least 40%, at least 50%, at least 60%, at least 70%, at least 80%, at least 90%, at least 100%, at least 150%, at least 200%, at least 350%, at least 300%, at least 350%, at least 400%, at least 450%, or at least 500% over the response in the absence of the first agent.

The term "dysregulation of apoptosis," as used herein, refers to any aberration in the ability of (e.g., predisposition) a cell to undergo cell death via apoptosis. Dysregulation of apoptosis is associated with or induced by a variety of conditions, including for example, autoimmune disorders (e.g., systemic lupus erythematosus, rheumatoid arthritis, graft-versus-host disease, myasthenia gravis, or Sjögren's syndrome), chronic inflammatory conditions (e.g., psoriasis, asthma or Crohn's disease), hyperproliferative disorders (e.g., tumors, B cell lymphomas, or T cell lymphomas), viral infections (e.g., herpes, papilloma, or HIV), and other conditions such as osteoarthritis and atherosclerosis. It should be noted that when the dysregulation is induced by or associated with a viral infection, the viral infection may or may not be detectable at the time dysregulation occurs or is observed. That is, viral-induced dysregulation can occur even after the disappearance of symptoms of viral infection.

The term "hyperproliferative disease," as used herein, refers to any condition in which a localized population of proliferating cells in an animal is not governed by the usual limitations of normal growth. Examples of hyperproliferative disorders include tumors, neoplasms, lymphomas and the like. A neoplasm is said to be benign if it does not undergo invasion or metastasis and malignant if it does either of these. A "metastatic" cell means that the cell can invade and destroy neighboring body structures. Hyperplasia is a form of cell proliferation involving an increase in cell number in a tissue or organ without significant alteration in structure or function. Metaplasia is a form of controlled cell growth in which one type of fully differentiated cell substitutes for another type of differentiated cell.

The pathological growth of activated lymphoid cells often results in an autoimmune disorder or a chronic inflammatory condition. As used herein, the term "autoimmune disorder" refers to any condition in which an organism produces antibodies or immune cells which recognize the organism's own molecules, cells or tissues. Non-limiting examples of autoimmune disorders include autoimmune hemolytic anemia, autoimmune hepatitis, Berger's disease or IgA nephropathy, celiac sprue, chronic fatigue syndrome, Crohn's disease, dermatomyositis, fibromyalgia, graft versus host disease, Grave's disease, Hashimoto's thyroiditis, idiopathic thrombocytopenia purpura, lichen planus, multiple sclerosis, myasthenia gravis, psoriasis, rheumatic fever, rheumatic arthritis, scleroderma, Sjögren's syndrome, systemic lupus erythematosus, type I diabetes, ulcerative colitis, vitiligo, and the like.

The term "neoplastic disease," as used herein, refers to any abnormal growth of cells being either benign (non-cancerous) or malignant (cancerous).

The term "anti-neoplastic agent," as used herein, refers to any compound that retards the proliferation, growth, or spread of a targeted (e.g., malignant) neoplasm.

The terms "prevent," "preventing," and "prevention," as used herein, refer to a decrease in the occurrence of pathological cells (e.g., hyperproliferative or neoplastic cells) in an animal. The prevention may be complete, e.g., the total absence of pathological cells in a subject. The prevention may also be partial, such that the occurrence of pathological cells in a subject is less than that which would have occurred without the present invention.

The term "synergistic," as used herein, refers to an effect obtained when gossypol acetic acid co-crystals or (−)-gossypol acetic acid co-crystals and a second agent are administered together (e.g., at the same time or one after the other) that is greater than the additive effect of gossypol acetic acid co-crystals or (−)-gossypol acetic acid co-crystals and the second agent when administered individually. The synergistic effect allows for lower doses of gossypol acetic acid co-crystals or (−)-gossypol acetic acid co-crystals and/or the second agent to be administered or provides greater efficacy at the same doses. The synergistic effect obtained can be at least 10%, at least 20%, at least 30%, at least 40%, at least 50%, at least 60%, at least 70%, at least 80%, at least 90%, at least 100%, at least 125%, at least 150%, at least 175%, at least 200%, at least 250%, at least 300%, at least 350%, at least 400%, or at least 500% more than the additive effect of the gossypol acetic acid co-crystals or (−)-gossypol acetic acid co-crystals and the second agent when administered individually. For example, with respect to the treatment of cancer, the synergistic effect can be a decrease in the rate of tumor growth, a decrease in tumor mass, a decrease in the number of metastases, an increase in time to tumor progression, or an increase in survival time. The co-administration of (−)-gossypol co-crystal and an anticancer agent may allow for the use of lower doses of (−)-gossypol co-crystal and/or the anticancer agent such that the cancer is effectively treated while avoiding any substantial toxicity to the subject.

The term "about," as used herein, includes the recited number +/−20%. Thus, "about 0.5" means 0.4 to 0.6.

Gossypol and (−)-gossypol have been shown to bind to Bcl-2 and Bcl-XL at the BH3 binding groove and to have significant anticancer activity (U.S. patent application Ser. No. 2003/0008924; 2004/0214902). Thus, compositions comprising gossypol acetic acid co-crystals or (−)-gossypol acetic acid co-crystals may be used to induce apoptosis and also potentiate the induction of apoptosis in response to apoptosis induction signals. It is contemplated that these compositions sensitize cells to inducers of apoptosis, including cells that are resistant to such inducers. The compositions of the present invention can be used to induce apoptosis in any disorder that can be treated, ameliorated, or prevented by the induction of apoptosis. Thus, the present invention provides compositions and methods for targeting animals characterized as overexpressing an anti-apoptotic Bcl-2 family protein. In some of the embodiments, the cells (e.g., cancer cells) show elevated expression levels of one or more anti-apoptotic Bcl-2 family proteins as compared to non-pathological samples (e.g., non-cancerous cells). In other embodiments, the cells operationally manifest elevated expression levels of anti-apoptotic Bcl-2 family proteins by virtue of executing the apoptosis program and dying in response to administration of an inhibiting effective amount of gossypol acetic acid co-crystals or (−)-gossypol acetic acid co-crystals, said response occurring, at least in part, due to the dependence in such cells on anti-apoptotic Bcl-2 family protein function for their survival.

In some embodiments, the compositions and methods of the present invention are used to treat diseased cells, tissues, organs, or pathological conditions and/or disease states in an animal (e.g., a mammalian subject including, but not limited to, humans and veterinary animals). In this regard, various diseases and pathologies are amenable to treatment or prophylaxis using the present methods and compositions. A non-limiting exemplary list of these diseases and conditions includes, but is not limited to, cancers such as breast cancer, prostate cancer, lymphoma, skin cancer, pancreatic cancer, colon cancer, melanoma, malignant melanoma, ovarian cancer, brain cancer, primary brain carcinoma, head-neck cancer, glioma, glioblastoma, liver cancer, bladder cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, acute myelogenous leukemia, chronic myelogenous leukemia, chronic granulocytic leukemia, acute granulocytic leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft-tissue sarcoma, osteogenic sarcoma, primary macroglobulinemia, and retinoblastoma, and the like; T and B cell mediated autoimmune diseases, inflammatory diseases, infections, hyperproliferative diseases, AIDS, degenerative conditions, vascular diseases, and the like. In some embodiments, the cancer cells being treated are metastatic. In other embodiments, the cancer cells being treated are resistant to anticancer agents.

In some embodiments, infections suitable for treatment with the compositions and methods of the present invention include, but are not limited to, infections caused by viruses, bacteria, fungi, parasites, mycoplasma, prions, and the like.

Some embodiments of the present invention provide methods for administering an effective amount of gossypol acetic acid co-crystals or gossypol acetic acid co-crystals and at least one additional therapeutic agent (including, but not limited to, chemotherapeutic agents, antineoplastic agents, antimicrobial agents, antiviral agents, antifungal agents, and anti-inflammatory agents) and/or therapeutic technique (e.g., surgical intervention, and/or radiotherapies). In some embodiments, the combination of gossypol acetic acid co-crystals or (−)-gossypol acetic acid co-crystals and one or more therapeutic agents will have a greater effect as compared to the administration of either compound alone. In other embodiments, the combination of gossypol acetic acid co-crystals or (−)-gossypol acetic acid co-crystals and one or more therapeutic agents is expected to result in a synergistic effect (i.e., more than additive) as compared to the administration of either one alone.

A number of suitable anticancer agents are contemplated for use in the methods of the present invention. Indeed, the present invention contemplates, but is not limited to, administration of numerous anticancer agents such as: agents that induce apoptosis; polynucleotides (e.g., anti-sense, ribozymes, siRNA); polypeptides (e.g., enzymes and antibodies); biological mimetics (e.g., gossypol or BH3 mimetics); agents that bind (e.g., oligomerize or complex) with a Bcl-2 family protein such as Bax; alkaloids; alkylating agents; antitumor antibiotics; antimetabolites; hormones; platinum compounds; monoclonal or polyclonal antibodies (e.g., antibodies conjugated with anticancer drugs, toxins, defensins), toxins; radionuclides; biological response modifiers (e.g., interferons (e.g., IFN-α) and interleukins (e.g., IL-2)); adoptive immunotherapy agents; hematopoietic growth factors; agents that induce tumor cell differentiation (e.g., all-trans-retinoic acid); gene therapy reagents (e.g., antisense therapy reagents and nucleotides); tumor vaccines; angiogenesis inhibitors; proteosome inhibitors: NF-KB modulators; anti-CDK compounds; HDAC inhibitors; and the like. Numerous other examples of chemotherapeutic compounds and anticancer therapies suitable for co-administration with the disclosed compounds are known to those skilled in the art.

In preferred embodiments, anticancer agents comprise agents that induce or stimulate apoptosis. Agents that induce apoptosis include, but are not limited to, radiation (e.g., X-rays, gamma rays, UV); tumor-derived growth factor ligands, receptors, and analogs; kinase inhibitors (e.g., epidermal growth factor receptor (EGFR) kinase inhibitor, vascular growth factor receptor (VGFR) kinase inhibitor, fibroblast growth factor receptor (FGFR) kinase inhibitor, platelet-derived growth factor receptor (PDGFR) kinase inhibitor, and Bcr-Abl kinase inhibitors (such as GLEEVEC)); antisense molecules; antibodies (e.g., HERCEPTIN, RITUXAN, ZEVALIN, BEXXAR, and AVASTIN); anti-estrogens (e.g., raloxifene and tamoxifen); anti-androgens (e.g., flutamide, bicalutamide, finasteride, aminoglutethamide, ketoconazole, and corticosteroids); cyclooxygenase 2 (COX-2) inhibitors (e.g., celecoxib, meloxicam, NS-398, and non-steroidal anti-inflammatory drugs); anti-inflammatory drugs (e.g., butazolidin, DECADRON, DELTASONE, dexamethasone, dexamethasone intensol, DEXONE, HEXADROL, hydroxychloroquine, METICORTEN, ORADEXON, ORASONE, oxyphenbutazone, PEDIAPRED, phenylbutazone, PLAQUENIL, prednisolone, prednisone, PRELONE, and TANDEARIL); and cancer chemotherapeutic drugs (e.g., irinotecan (CAMPTOSAR), CPT-11, fludarabine (FLUDARA), dacarbazine, dexamethasone, mitoxantrone, MYLOTARG, VP-16, cisplatin, carboplatin, oxaliplatin, 5-FU, doxorubicin, gemcitabine, bortezomib, gefitinib, bevacizumab, TAXOTERE or TAXOL); cellular signaling molecules; ceramides and cytokines; staurosporine, and the like.

In still other embodiments, the compositions and methods of the present invention provide gossypol acetic acid co-crystals or (−)-gossypol acetic acid co-crystals and at least one anti-hyperproliferative or antineoplastic agent; e.g., selected from alkylating agents, antimetabolites, and natural products (e.g., herbs and other plant and/or animal derived compounds).

Alkylating agents suitable for use in the present compositions and methods include, but are not limited to: 1) nitrogen mustards (e.g., mechlorethamine, cyclophosphamide, ifosfamide, melphalan (L-sarcolysin); and chlorambucil); 2) ethyleniminines and methylmelamines (e.g., hexamethylmelamine and thiotepa); 3) alkyl sulfonates (e.g., busulfan); 4) nitrosoureas (e.g., carmustine (BCNU); lomustine (CCNU); semustine (methyl-CCNU); and streptozocin (streptozotocin)); and 5) triazenes (e.g., dacarbazine (dimethyltriazenoimid-azolecarboxamide).

In some embodiments, antimetabolites suitable for use in the present compositions and methods include, but are not limited to: 1) folic acid analogs (e.g., methotrexate (amethopterin)); 2) pyrimidine analogs (e.g., fluorouracil (5-fluorouracil), floxuridine (fluorode-oxyuridine), and cytarabine (cytosine arabinoside)); and 3) purine analogs (e.g., mercaptopurine (6-mercaptopurine), thioguanine (6-thioguanine), and pentostatin (2'-deoxycoformycin)).

In still further embodiments, chemotherapeutic agents suitable for use in the compositions and methods of the present invention include, but are not limited to: 1) vinca alkaloids (e.g., vinblastine, vincristine); 2) epipodophyllotoxins (e.g., etoposide and teniposide); 3) antibiotics (e.g., dactinomycin (actinomycin D), daunorubicin (daunomycin; rubidomycin), doxorubicin, bleomycin, plicamycin (mithramycin), and mitomycin (mitomycin C)); 4) enzymes (e.g., L-asparaginase); 5) biological response modifiers (e.g., interferon-alfa); 6) platinum coordinating complexes (e.g., cisplatin and carboplatin); 7) anthracenediones (e.g., mitoxantrone); 8) substituted ureas (e.g., hydroxyurea); 9) methylhydrazine derivatives (e.g., procarbazine (N-methylhydrazine)); 10) adrenocortical suppressants (e.g., mitotane (o,p'-DDD) and aminoglutethimide); 11) adrenocorticosteroids (e.g., prednisone); 12) progestins (e.g., hydroxyprogesterone caproate, medroxyprogesterone acetate, and megestrol acetate); 13) estrogens (e.g., diethylstilbestrol and ethinyl estradiol); 14) antiestrogens (e.g., tamoxifen); 15) androgens (e.g., testosterone propionate and fluoxymesterone); 16) antiandrogens (e.g., flutamide): and 17) gonadotropin-releasing hormone analogs (e.g., leuprolide).

Any oncolytic agent that is routinely used in a cancer therapy context finds use in the compositions and methods of the present invention. For example, the U.S. Food and Drug Administration maintains a formulary of oncolytic agents approved for use in the United States. International counterpart agencies to the U.S.F.D.A. maintain similar formularies. Table 1 provides a list of exemplary antineoplastic agents approved for use in the U.S. Those skilled in the art will appreciate that the "product labels" required on all U.S. approved chemotherapeutics describe approved indications, dosing information, toxicity data, and the like, for the exemplary agents.

TABLE 1

| | | |
|---|---|---|
| Aldesleukin (des-alanyl-1, serine-125 human interleukin-2) | Proleukin | Chiron Corp., Emeryville, CA |
| Alemtuzumab (IgG1κ anti CD52 antibody) | Campath | Millennium and ILEX Partners, LP, Cambridge, MA |
| Alitretinoin (9-cis-retinoic acid) | Panretin | Ligand Pharmaceuticals, Inc., San Diego CA |
| Allopurinol (1,5-dihydro-4 H -pyrazolo[3,4-d]pyrimidin-4-one monosodium salt) | Zyloprim | GlaxoSmithKline, Research Triangle Park, NC |
| Altretamine (N,N,N',N',N",N",-hexamethyl-1,3,5-triazine-2, 4, 6-triamine) | Hexalen | US Bioscience, West Conshohocken, PA |
| Amifostine (ethanethiol, 2-[(3-aminopropyl)amino]-, dihydrogen phosphate (ester)) | Ethyol | US Bioscience |
| Anastrozole (1,3-Benzenediacetonitrile, a, a, a', a'-tetramethyl-5-(1H-1,2,4-triazol-1-ylmethyl)) | Arimidex | AstraZeneca Pharmaceuticals, LP, Wilmington, DE |
| Arsenic trioxide | Trisenox | Cell Therapeutic, Inc., Seattle, WA |
| Asparaginase (L-asparagine amidohydrolase, type EC-2) | Elspar | Merck & Co., Inc., Whitehouse Station, NJ |
| BCG Live (lyophilized preparation of an attenuated strain of *Mycobacterium bovis* (Bacillus Calmette-Gukin [BCG], substrain Montreal) | TICE BCG | Organon Teknika, Corp., Durham, NC |
| bexarotene capsules (4-[1-(5,6,7,8-tetrahydro-3,5,5,8,8-pentamethyl-2-napthalenyl) ethenyl] benzoic acid) | Targretin | Ligand Pharmaceuticals |
| bexarotene gel | Targretin | Ligand Pharmaceuticals |

TABLE 1-continued

| | | |
|---|---|---|
| Bleomycin (cytotoxic glycopeptide antibiotics produced by *Streptomyces verticillus*; bleomycin $A_2$ and bleomycin $B_2$) | Blenoxane | Bristol-Myers Squibb Co., NY, NY |
| Capecitabine (5'-deoxy-5-fluoro-N-[(pentyloxy)carbonyl]-cytidine) | Xeloda | Roche |
| Carboplatin (platinum, diammine [1,1-cyclobutanedicarboxylato(2-)-0, 0']-,(SP-4-2)) | Paraplatin | Bristol-Myers Squibb |
| Carmustine (1,3-bis(2-chloroethyl)-1-nitrosourea) | BCNU, BiCNU | Bristol-Myers Squibb |
| Carmustine with Polifeprosan 20 Implant | Gliadel Wafer | Guilford Pharmaceuticals, Inc., Baltimore, MD |
| Celecoxib (as 4-[5-(4-methylphenyl)-3- (trifluoromethyl)-1H-pyrazol-1-yl]benzenesulfonamide) | Celebrex | Searle Pharmaceuticals, England |
| Chlorambucil (4-[bis(2chloroethyl)amino]benzenebutanoic acid) | Leukeran | GlaxoSmithKline |
| Cisplatin ($PtCl_2H_6N_2$) | Platinol | Bristol-Myers Squibb |
| Cladribine (2-chloro-2'-deoxy-b-D-adenosine) | Leustatin, 2-CdA | R. W. Johnson Pharmaceutical Research Institute, Raritan, NJ |
| Cyclophosphamide (2-[bis(2-chloroethyl)amino] tetrahydro-2H-13,2-oxazaphosphorine 2-oxide monohydrate) | Cytoxan, Neosar | Bristol-Myers Squibb |
| Cytarabine (1-b-D-Arabinofuranosylcytosine, $C_9H_{13}N_3O_5$) | Cytosar-U | Pharmacia & Upjohn Company |
| cytarabine liposomal | DepoCyt | Skye Pharmaceuticals, Inc., San Diego, CA |
| Dacarbazine (5-(3,3-dimethyl-l-triazeno)-imidazole-4-carboxamide (DTIC)) | DTIC-Dome | Bayer AG, Leverkusen, Germany |
| Dactinomycin, actinomycin D (actinomycin produced by *Streptomyces parvullus*, $C_{62}H_{86}N_{12}O_{16}$) | Cosmegen | Merck |
| Darbepoetin alfa (recombinant peptide) | Aranesp | Amgen, Inc., Thousand Oaks, CA |
| daunorubicin liposomal ((8S-cis)-8-acetyl-10-[(3-amino-2,3,6-trideoxy-á-L-lyxo-hexopyranosyl)oxy]-7,8,9,10-tetrahydro-6,8,11-trihydroxy-1-methoxy-5,12-naphthacenedione hydrochloride) | DanuoXome | Nexstar Pharmaceuticals, Inc., Boulder, CO |
| Daunorubicin HCl, daunomycin ((1 S ,3 S)-3-Acetyl-1,2,3,4,6,11-hexahydro-3,5,12-trihydroxy-10-methoxy-6,11-dioxo-1-naphthacenyl 3-amino-2,3,6-trideoxy-(alpha)-L-lyxo-hexopyranoside hydrochloride) | Cerubidine | Wyeth Ayerst, Madison, NJ |
| Denileukin diftitox (recombinant peptide) | Ontak | Seragen, Inc., Hopkinton, MA |
| Dexrazoxane ((S)-4,4'-(1-methyl-1,2-ethanediyl)bis-2,6-piperazinedione) | Zinecard | Pharmacia & Upjohn Company |
| Docetaxel ((2R,3S)-N-carboxy-3-phenylisoserine, N-tert-butyl ester, 13-ester with 5b-20-epoxy-12a,4,7b,10b,13a-hexahydroxytax- 11-en-9-one 4-acetate 2-benzoate, trihydrate) | Taxotere | Aventis Pharmaceuticals, Inc., Bridgewater, NJ |
| Doxorubicin HCl (8S,10S)-10-[(3-amino-2,3,6-trideoxy-a-L-lyxo-hexopyranosyl)oxy] -8-glycolyl-7,8,9,10-tetrahydro-6,8,11-trihydroxy-1-methoxy-5,12-naphthacenedione hydrochloride) | Adriamycin, Rubex | Pharmacia & Upjohn Company |
| doxorubicin | Adriamycin PFS Intravenous injection | Pharmacia & Upjohn Company |
| doxorubicin liposomal | Doxil | Sequus Pharmaceuticals, Inc., Menlo park, CA |
| dromostanolone propionate (17b-Hydroxy-2a-methyl-5a-androstan-3-one propionate) | Dromostanolone | Eli Lilly & Company, Indianapolis, IN |
| dromostanolone propionate | Masterone injection | Syntex, Corp., Palo Alto, CA |
| Elliott's B Solution | Elliott's B Solution | Orphan Medical, Inc |
| Epirubicin ((8S-cis)-10-[(3-amino-2,3,6-trideoxy-a-L-arabino-hexopyranosyl)oxy]-7,8,9,10-tetrahydro-6,8,11-trihydroxy-8-(hydroxyacetyl)-1-methoxy-5,12-naphthacenedione hydrochloride) | Ellence | Pharmacia & Upjohn Company |
| Epoetin alfa (recombinant peptide) | Epogen | Amgen, Inc |

TABLE 1-continued

| | | |
|---|---|---|
| Estramustine (estra-1,3,5(10)-triene-3,17-diol(17(beta))-, 3-[bis(2-chloroethyl)carbamate]17-(dihydrogen phosphate), disodium salt, monohydrate, or estradiol 3-[bis(2-chloroethyl)carbamate] 17-(dihydrogen phosphate), disodium salt, monohydrate) | Emcyt | Pharmacia & Upjohn Company |
| Etoposide phosphate (4'-Demethylepipodophyllotoxin 9-[4,6-O-(R)-ethylidene-(beta)-D-glucopyranoside], 4'-(dihydrogen phosphate)) | Etopophos | Bristol-Myers Squibb |
| etoposide, VP-16 (4'-demethylepipodophyllotoxin 9-[4,6-0-(R)-ethylidene-(beta)-D-glucopyranoside]) | Vepesid | Bristol-Myers Squibb |
| Exemestane (6-methylenandrosta-1,4-diene-3, 17-dione) | Aromasin | Pharmacia & Upjohn Company |
| Filgrastim (r-metHuG-CSF) | Neupogen | Amgen, Inc |
| floxuridine (intraarterial) (2'-deoxy-5-fluorouridine) | FUDR | Roche |
| Fludarabine (fluorinated nucleotide analog of the antiviral agent vidarabine, 9-b -D-arabinofuranosyladenine(ara-A)) | Fludara | Berlex Laboratories, Inc., Cedar Knolls, NJ |
| Fluorouracil, 5-FU (5-fluoro-2,4(1H,3H)-pyrimidinedione) | Adrucil | ICN Pharmaceuticals, Inc., Humacao, Puerto Rico |
| Fulvestrant (7-alpha-[9-(4,4,5,5,5-penta fluoropentylsulphinyl) nonyl]estra-1,3,5-(10)- triene-3,17-beta-diol) | Faslodex | IPR Pharmaceuticals, Guayama, Puerto Rico |
| Gemcitabine (2'-deoxy-2', 2'-difluorocytidine monohydrochloride (b-isomer)) | Gemzar | Eli Lilly |
| Gemtuzumab Ozogamicin (anti-CD33 hP67.6) | Mylotarg | Wyeth Ayerst |
| Goserelin acetate (acetate salt of [D-Ser(But)$^6$,Azgly$^{10}$]LHRH; pyro-Glu-His-Trp-Ser-Tyr-D-Ser(But)-Leu-Arg-Pro-Azgly-NH2 acetate [$C_{59}H_{84}N_{18}O_{14}$ •$(C_2H_4O_2)_x$ | Zoladex Implant | AstraZeneca Pharmaceuticals |
| Hydroxyurea | Hydrea | Bristol-Myers Squibb |
| Ibritumomab Tiuxetan (immunoconjugate resulting from a thiourea covalent bond between the monoclonal antibody Ibritumomab and the linker-chelator tiuxetan [N-[2-bis(carboxymethyl)amino]-3-(p-isothiocyanatophenyl)-propyl]-[N-[2-bis(carboxymethyl)amino]-2-(methyl) -ethyl]glycine) | Zevalin | Biogen IDEC, Inc., Cambridge MA |
| Idarubicin (5, 12-Naphthacenedione, 9-acetyl-7-[(3-amino-2,3,6-trideoxy-(alpha)-L- lyxo - hexopyranosyl)oxy]-7,8,9,10-tetrahydro-6,9,11-trihydroxyhydrochloride, (7S- cis)) | Idamycin | Pharmacia & Upjohn Company |
| Ifosfamide (3-(2-chloroethyl)-2-[(2-chloroethyl)amino]tetrahydro-2H-1,3,2-oxazaphosphorine 2-oxide) | IFEX | Bristol-Myers Squibb |
| Imatinib Mesilate (4-[(4-Methyl-1-piperazinyl)methyl]-N-[4-methyl-3-[[4-(3-pyridinyl)-2-pyrimidinyl]amino]-phenyl]benzamide methanesulfonate) | Gleevec | Novartis AG, Basel, Switzerland |
| Interferon alfa-2a (recombinant peptide) | Roferon-A | Hoffmann-La Roche, Inc., Nutley, NJ |
| Interferon alfa-2b (recombinant peptide) | Intron A (Lyophilized Betaseron) | Schering AG, Berlin, Germany |
| Irinotecan HCl ((4S)-4,11-diethyl-4-hydroxy-9-[(4- piperi-dinopiperidino)carbonyloxy]-1H-pyrano[3', 4': 6,7] indolizino[1,2-b] quinoline-3,14(4H, 12H) dione hydrochloride trihydrate) | Camptosar | Pharmacia & Upjohn Company |
| Letrozole (4,4'-(1H-1,2,4 - Triazol-1-ylmethylene) dibenzonitrile) | Femara | Novartis |
| Leucovorin (L-Glutamic acid, N[4[[(2amino-5-formyl-1,4,5,6,7,8 hexahydro4oxo6-pteridinyl)methyl]amino]benzoyl], calcium salt (1:1)) | Wellcovorin, Leucovorin | Immunex, Corp., Seattle, WA |
| Levamisole HCl ((-)-(S)-2,3,5, 6-tetrahydro-6-phenylimidazo [2,1-b] thiazole monohydrochloride $C_{11}H_{12}N_2S$•HCl) | Ergamisol | Janssen Research Foundation, Titusville, NJ |
| Lomustine (1-(2-chloro-ethyl)-3-cyclohexyl-1-nitrosourea) | CeeNU | Bristol-Myers Squibb |

TABLE 1-continued

| | | |
|---|---|---|
| Mechlorethamine, nitrogen mustard (2-chloro-N-(2-chloroethyl)-N-methylethanamine hydrochloride) | Mustargen | Merck |
| Megestrol acetate 17α( acetyloxy)- 6- methylpregna- 4,6- diene-3,20- dione | Megace | Bristol-Myers Squibb |
| Melphalan, L-PAM (4-[bis(2-chloroethyl) amino]-L-phenylalanine) | Alkeran | GlaxoSmithKline |
| Mercaptopurine, 6-MP (1,7-dihydro-6 H -purine-6-thione monohydrate) | Purinethol | GlaxoSmithKline |
| Mesna [sodium 2-mercaptoethane sulfonate) | Mesnex | Asta Medica |
| Methotrexate (N-[4-[[(2,4-diamino-6-pteridinyl)methyl]methylamino]benzoyl]-L-glutamic acid) | Methotrexate | Lederle Laboratories |
| Methoxsalen (9-methoxy-7H-furo[3,2-g][1]-benzopyran-7-one) | Uvadex | Therakos, Inc., Way Exton, Pa |
| Mitomycin C | Mutamycin | Bristol-Myers Squibb |
| mitomycin C | Mitozytrex | SuperGen, Inc., Dublin, CA |
| Mitotane (1,1-dichloro-2-(o-chlorophenyl)-2-(p-chlorophenyl) ethane) | Lysodren | Bristol-Myers Squibb |
| Mitoxantrone (1,4-dihydroxy-5,8-bis[[2- [(2-hydroxyethyl)amino]ethyl]amino]-9,10-anthracenedione dihydrochloride) | Novantrone | Immunex Corporation |
| Nandrolone phenpropionate | Durabolin-50 | Organon, Inc., West Orange, NJ |
| Nofetumomab | Verluma | Boehringer Ingelheim Pharma KG, Germany |
| Oprelvekin (IL-11) | Neumega | Genetics Institute, Inc., Alexandria, VA |
| Oxaliplatin (cis-[(1R,2R)-1,2-cyclohexanediamine-N,N'] [oxalato(2-)-O,0'] platinum) | Eloxatin | Sanofi Synthelabo, Inc., NY, NY |
| Paclitaxel (5β, 20-Epoxy-1,2a, 4,7β, 10β, 13a-hexahydrotax-11-en-9-one 4,10-diacetate 2-benzoate 13-ester with (2R, 3 S)- N-benzoyl-3-phenylisoserine) | TAXOL | Bristol-Myers Squibb |
| Pamidronate (phosphonic acid (3-amino-1-hydroxypropylidene) bis-, disodium salt, pentahydrate, (APD)) | Aredia | Novartis |
| Pegademase ((monomethoxypolyethylene glycol succinimidyl) 11 - 17 -adenosine deaminase) | Adagen (Pegademase Bovine) | Enzon Pharmaceuticals, Inc., Bridgewater, NJ |
| Pegaspargase (monomethoxypolyethylene glycol succinimidyl L-asparaginase) | Oncaspar | Enzon |
| Pegfilgrastim (covalent conjugate of recombinant methionyl human G-CSF (Filgrastim) and monomethoxypolyethylene glycol) | Neulasta | Amgen, Inc |
| Pentostatin | Nipent | Parke-Davis Pharmaceutical Co., Rockville, MD |
| Pipobroman | Vercyte | Abbott Laboratories, Abbott Park, IL |
| Plicamycin, Mithramycin (antibiotic produced by *Streptomyces plicatus*) | Mithracin | Pfizer, Inc., NY, NY |
| Porfimer sodium | Photofrin | QLT Phototherapeutics, Inc., Vancouver, Canada |
| Procarbazine (N-isopropyl-μ-(2-methylhydrazino)-p-toluamide monohydrochloride) | Matulane | Sigma Tau Pharmaceuticals, Inc., Gaithersburg, MD |
| Quinacrine (6-chloro-9-( 1 -methyl-4-diethyl-amine) butylamino-2-methoxyacridine) | Atabrine | Abbott Labs |
| Rasburicase (recombinant peptide) | Elitek | Sanofi-Synthelabo, Inc., |
| Rituximab (recombinant anti-CD20 antibody) | Rituxan | Genentech, Inc., South San Francisco, CA |
| Sargramostim (recombinant peptide) | Prokine | Immunex Corp |
| Streptozocin (streptozocin 2 -deoxy - 2 -[[(methylnitrosoamino)carbonyl]amino] - a(and b )-D - glucopyranose and 220 mg citric acid anhydrous) | Zanosar | Pharmacia & Upjohn Company |
| Talc ($Mg_3Si_4O_{10}(OH)_2$) | Sclerosol | Bryan, Corp., Woburn, MA |
| Tamoxifen ((Z)2-[4-(1,2-diphenyl-1-butenyl) phenoxy]-N, N-dimethylethanamine 2-hydroxy-1,2,3-propanetricarboxylate (1:1)) | Nolvadex | AstraZeneca Pharmaceuticals |

TABLE 1-continued

| | | |
|---|---|---|
| Temozolomide (3,4-dihydro-3-methyl-4-oxoimidazo[5,1-d]-as-tetrazine-8-carboxamide) | Temodar | Schering |
| teniposide, VM-26 (4'-demethylepipodophyllotoxin 9-[4,6-0-(R)-2-thenylidene-(beta)-D-glucopyranoside]) | Vumon | Bristol-Myers Squibb |
| Testolactone (13-hydroxy-3-oxo-13,17-secoandrosta-1,4-dien-17-oic acid [dgr]-lactone) | Teslac | Bristol-Myers Squibb |
| Thioguanine, 6-TG (2-amino-1,7-dihydro-6 H - purine-6-thione) | Thioguanine | GlaxoSmithKline |
| Thiotepa (Aziridine, 1,1',1''-phosphinothioylidynetris-, or Tris (1-aziridinyl) phosphine sulfide) | Thioplex | Immunex Corporation |
| Topotecan HCl ((S)-10-[(dimethylamino) methyl]-4-ethyl-4,9-dihydroxy-1H-pyrano[3', 4': 6,7] indolizino [1,2-b] quinoline-3,14-(4H,12H)-dione monohydrochloride) | Hycamtin | GlaxoSmithKline |
| Toremifene (2-(p-[(Z)-4-chloro-1,2-diphenyl-1-butenyl]-phenoxy)-N,N-dimethylethylamine citrate (1:1)) | Fareston | Roberts Pharmaceutical Corp., Eatontown, NJ |
| Tositumomab, I 131 Tositumomab (recombinant murine immunotherapeutic monoclonal IgG$_{2a}$ lambda anti-CD20 antibody (I 131 is a radioimmunotherapeutic antibody)) | Bexxar | Corixa Corp., Seattle, WA |
| Trastuzumab (recombinant monoclonal IgG$_1$ kappa anti-HER2 antibody) | Herceptin | Genentech, Inc |
| Tretinoin, ATRA (all-trans retinoic acid) | Vesanoid | Roche |
| Uracil Mustard | Uracil Mustard Capsules | Roberts Labs |
| Valrubicin, N-trifluoroacetyladriamycin-14-valerate ((2S-cis)-2-[1,2,3,4,6,11-hexahydro-2,5,12-trihydroxy-7 methoxy-6,11-dioxo-[[4 2,3,6-trideoxy-3-[(trifluoroacetyl)-amino-α-L-lyxo-hexopyranosyl]oxyl]-2-naphthacenyl]-2-oxoethyl pentanoate) | Valstar | Anthra --> Medeva |
| Vinblastine, Leurocristine ($C_{46}H_{56}N_4O_{10} \bullet H_2SO_4$) | Velban | Eli Lilly |
| Vincristine ($C_{46}H_{56}N_4O_{10} \bullet H_2SO_4$) | Oncovin | Eli Lilly |
| Vinorelbine (3',4'-didehydro-4'-deoxy-C'-norvincaleukoblastine [R-(R*,R*)-2,3-dihydroxybutanedioate (1:2)(salt)]) | Navelbine | GlaxoSmithKline |
| Zoledronate, Zoledronic acid ((1-Hydroxy-2-imidazol-1-yl-phosphonoethyl) phosphonic acid monohydrate) | Zometa | Novartis |

Anticancer agents further include compounds which have been identified to have anticancer activity but are not currently approved by the U.S. Food and Drug Administration or other counterpart agencies or are undergoing evaluation for new uses. Examples include, but are not limited to, 3-AP, 12-O-tetradecanoylphorbol-13-acetate, 17AAG, 852A, ABI-007, ABR-217620, ABT-751, ADI-PEG 20, AE-941, AG-013736, AGRO100, alanosine, AMG 706, antibody G250, antineoplastons, AP23573, apaziquone, APC8015, atiprimod, ATN-161, atrasenten, azacitidine, BB-10901, BCX-1777, bevacizumab, BG00001, bicalutamide, BMS 247550, bortezomib, bryostatin-1, buserelin, calcitriol, CCI-779, CDB-2914, cefixime, cetuximab, CG0070, cilengitide, clofarabine, combretastatin A4 phosphate, CP-675,206, CP-724,714, CpG 7909, curcumin, decitabine, DENSPM, doxercalciferol, E7070, E7389, ecteinascidin 743, efaproxiral, eflornithine, EKB-569, enzastaurin, erlotinib, exisulind, fenretinide, flavopiridol, fludarabine, flutamide, fotemustine, FR901228, G17DT, galiximab, gefitinib, genistein, glufosfamide, GTI-2040, histrelin, HKI-272, homoharringtonine, HSPPC-96, hu14.18-interleukin-2 fusion protein, HuMax-CD4, iloprost, imiquimod, infliximab, interleukin-12, IPI-504, irofulven, ixabepilone, lapatinib, lenalidomide, lestaurtinib, leuprolide, LMB-9 immunotoxin, lonafamib, luniliximab, mafosfamide, MB07133, MDX-010, MLN2704, monoclonal antibody 3F8, monoclonal antibody J591, motexafin, MS-275, MVA-MUC1-IL2, nilutamide, nitrocamptothecin, nolatrexed dihydrochloride, nolvadex, NS-9, O6-benzylguanine, oblimersen sodium, ONYX-015, oregovomab, OSI-774, panitumumab, paraplatin, PD-0325901, pemetrexed, PHY906, pioglitazone, pirfenidone, pixantrone, PS-341, PSC 833, PXD101, pyrazoloacridine, R115777, RAD001, ranpirnase, rebeccamycin analogue, rhuAngiostatin protein, rhuMab 2C4, rosiglitazone, rubitecan, S-1, S-8184, satraplatin, SB-, 15992, SGN-0010, SGN-40, sorafenib, SR31747A, ST1571, SU011248, suberoylanilide hydroxamic acid, suramin, talabostat, talampanel, tariquidar, temsirolimus, TGFa-PE38 immunotoxin, thalidomide, thymalfasin, tipifarnib, tirapazamine, TLK286, trabectedin, trimetrexate glucuronate, TroVax, UCN-1, valproic acid, vinflunine, VNP40101M, volociximab, vorinostat, VX-680, ZD1839, ZD6474, zileuton, and zosuquidartrihydrochloride.

For a more detailed description of anticancer agents and other therapeutic agents, those skilled in the art are referred to any number of instructive manuals including, but not limited to, the Physician's Desk Reference and to Goodman and Gilman's "Pharmacological Basis of Therapeutics" tenth edition, Eds. Hardman et al., 2001.

The present invention provides methods for administering gossypol acetic acid co-crystals or (−)-gossypol acetic acid co-crystals with radiation therapy. The invention is not limited by the types, amounts, or delivery and administration systems used to deliver the therapeutic dose of radiation to an animal. For example, the animal may receive photon radiotherapy, particle beam radiation therapy, radioisotope therapy (e.g., radioconjugates with monoclonal antibodies), other types of radiotherapies, and combinations thereof. In some embodiments, the radiation is delivered to the animal using a linear accelerator. In still other embodiments, the radiation is delivered using a gamma knife.

The source of radiation can be external or internal to the animal. External radiation therapy is most common and involves directing a beam of high-energy radiation to a tumor site through the skin using, for instance, a linear accelerator. While the beam of radiation is localized to the tumor site, it is nearly impossible to avoid exposure of normal, healthy tissue. However, external radiation is usually well tolerated by patients. Internal radiation therapy involves implanting a radiation-emitting source, such as beads, wires, pellets, capsules, particles, and the like, inside the body at or near the tumor site including the use of delivery systems that specifically target cancer cells (e.g., using particles attached to cancer cell binding ligands). Such implants can be removed following treatment, or left in the body inactive. Types of internal radiation therapy include, but are not limited to, brachytherapy, interstitial irradiation, intracavity irradiation, radioimmunotherapy, and the like.

The animal may optionally receive radiosensitizers (e.g., metronidazole, misonidazole, intra-arterial Budr, intravenous iododeoxyuridine (IudR), nitroimidazole, 5-substituted-4-nitroimidazoles, 2H-isoindolediones, [[(2-bromoethyl)-amino]methyl]-nitro-1H-imidazole-1-ethanol, nitroaniline derivatives, DNA-affinic hypoxia selective cytotoxins, halogenated DNA ligand, 1,2,4 benzotriazine oxides, 2-nitroimidazole derivatives, fluorine-containing nitroazole derivatives, benzamide, nicotinamide, acridine-intercalator, 5-thiotretrazole derivative, 3-nitro-1,2,4-triazole, 4,5-dinitroimidazole derivative, hydroxylated texaphrins, cisplatin, mitomycin, tiripazamine, nitrosourea, mercaptopurine, methotrexate, fluorouracil, bleomycin, vincristine, carboplatin, epirubicin, doxorubicin, cyclophosphamide, vindesine, etoposide, paclitaxel, heat (hyperthermia), and the like), radioprotectors (e.g., cysteamine, aminoalkyl dihydrogen phosphorothioates, amifostine (WR 2721), IL-1, IL-6, and the like). Radiosensitizers enhance the killing of tumor cells. Radioprotectors protect healthy tissue from the harmful effects of radiation.

Any type of radiation can be administered to a patient, so long as the dose of radiation is tolerated by the patient without unacceptable negative side-effects. Suitable types of radiotherapy include, for example, ionizing (electromagnetic) radiotherapy (e.g., X-rays or gamma rays) or particle beam radiation therapy (e.g., high linear energy radiation). Ionizing radiation is defined as radiation comprising particles or photons that have sufficient energy to produce ionization, i.e., gain or loss of electrons (as described in, for example, U.S. Pat. No. 5,770,581 incorporated herein by reference in its entirety). The effects of radiation can be at least partially controlled by the clinician. The dose of radiation is preferably fractionated for maximal target cell exposure and reduced toxicity.

The total dose of radiation administered to an animal preferably is about 0.01 Gray (Gy) to about 100 Gy. More preferably, about 10 Gy to about 65 Gy (e.g., about 15 Gy, 20 Gy, 25 Gy, 30 Gy, 35 Gy, 40 Gy, 45 Gy, 50 Gy, 55 Gy, or 60 Gy) are administered over the course of treatment. While in some embodiments a complete dose of radiation can be administered over the course of one day, the total dose is ideally fractionated and administered over several days. Desirably, radiotherapy is administered over the course of at least about 3 days, e.g., at least 5, 7, 10, 14, 17, 21, 25, 28, 32, 35, 38, 42, 46, 52, or 56 days (about 1-8 weeks). Accordingly, a daily dose of radiation will comprise approximately 1-5 Gy (e.g., about 1 Gy, 1.5 Gy, 1.8 Gy, 2 Gy, 2.5 Gy, 2.8 Gy, 3 Gy, 3.2 Gy, 3.5 Gy, 3.8 Gy, 4 Gy, 4.2 Gy, or 4.5 Gy), preferably 1-2 Gy (e.g., 1.5-2 Gy). The daily dose of radiation should be sufficient to induce destruction of the targeted cells. If stretched over a period, radiation preferably is not administered every day, thereby allowing the animal to rest and the effects of the therapy to be realized. For example, radiation commonly is administered on 5 consecutive days, and not administered on 2 days, for each week of treatment, thereby allowing 2 days of rest per week. However, radiation can be administered 1 day/week, 2 days/week, 3 days/week, 4 days/week, 5 days/week, 6 days/week, or all 7 days/week, depending on the animal's responsiveness and any potential side effects. Radiation therapy can be initiated at any time in the therapeutic period. Preferably, radiation is initiated in week 1 or week 2, and is administered for the remaining duration of the therapeutic period. For example, radiation is administered in weeks 1-6 or in weeks 2-6 of a therapeutic period comprising 6 weeks for treating, for instance, a solid tumor. Alternatively, radiation is administered in weeks 1-5 or weeks 2-5 of a therapeutic period comprising 5 weeks. These exemplary radiotherapy administration schedules are not intended, however, to limit the present invention.

Antimicrobial therapeutic agents may also be used as therapeutic agents in the present invention. Any agent that can kill, inhibit, or otherwise attenuate the function of microbial organisms may be used, as well as any agent contemplated to have such activities. Antimicrobial agents include, but are not limited to, natural and synthetic antibiotics, antibodies, inhibitory proteins (e.g., defensins), antisense nucleic acids, membrane disruptive agents and the like, used alone or in combination. Indeed, any type of antibiotic may be used including, but not limited to, antibacterial agents, antiviral agents, antifungal agents, and the like.

In some embodiments of the present invention, gossypol acetic acid co-crystals or (−)-gossypol acetic acid co-crystals and one or more therapeutic agents or anticancer agents are administered to an animal under one or more of the following conditions: at different periodicities, at different durations, at different concentrations, by different administration routes, etc. In some embodiments, gossypol acetic acid co-crystals or (−)-gossypol acetic acid co-crystals are administered prior to the therapeutic or anticancer agent, e.g., 0.5, 1, 2 3, 4, 5, 10, 12, or 18 hours, 1, 2, 3, 4, 5, or 6 days, 1, 2, 3, or 4 weeks prior to the administration of the therapeutic or anticancer agent. In some embodiments, gossypol acetic acid co-crystals or (−)-gossypol acetic acid co-crystals are administered after the therapeutic or anticancer agent, e.g., 0.5, 1, 2 3, 4, 5, 10, 12, or 18 hours, 1, 2, 3, 4, 5, or 6 days, 1, 2, 3, or 4 weeks after the administration of the anticancer agent. In some embodiments, gossypol acetic acid co-crystals or (−)-gossypol acetic acid co-crystals and the therapeutic or anticancer agent are administered concurrently but on different schedules, e.g., gossypol acetic acid co-crystals or (−)-gossypol acetic acid co-crystals are administered daily while the therapeutic or anticancer agent is administered once a week, once every two weeks, once every three weeks, or once every four weeks. In other embodiments, gossypol acetic acid co-crystals or (−)-gossypol acetic acid co-crystals are administered once a week while the therapeutic or anticancer agent is administered daily, once a week, once every two weeks, once every three weeks, or once every four weeks.

Pharmaceutical compositions can be produced by admixing gossypol acetic acid co-crystals or (−)-gossypol acetic acid co-crystals in a therapeutically effective amount to induce apoptosis in cells or to sensitize cells to inducers of apoptosis with a pharmaceutically acceptable carrier. The novel pharmaceutical compositions of the present invention comprise intact gossypol acetic acid co-crystals or (−)-gossypol acetic acid co-crystals. In some embodiments, the pharmaceutical compositions comprise gossypol acetic acid co-crystals or (−)-gossypol acetic acid co-crystals in combination with a liquid in which the co-crystals are substantially insoluble (e.g., water) such that a suspension is formed.

Compositions within the scope of this invention include all compositions wherein the compositions of the present invention are contained in an amount which is effective to achieve its intended purpose. While individual needs vary, determination of optimal ranges of effective amounts of each component is within the skill of the art. Typically, the compositions may be administered to mammals, e.g. humans, orally at a dose of 0.0025 to 50 mg/kg, or an equivalent amount of the pharmaceutically acceptable salt thereof, per day of the body weight of the mammal being treated for disorders responsive to induction of apoptosis. Preferably, about 0.01 to about 10 mg/kg is orally administered to treat, ameliorate, or prevent such disorders. For example, the compositions may be administered at a dose of 5, 10, 20, 30, 40, 50, 60, 70, 80, 90, 100, 110, 120, 130, 140, 150, 160, 170, 180, 190, or 200 mg. For intramuscular injection, the dose is generally about one-half of the oral dose. For example, a suitable intramuscular dose would be about 0.000125 to about 25 mg/kg, and most preferably, from about 0.005 to about 5 mg/kg.

The unit oral dose may comprise from about 0.01 to about 200 mg, preferably about 0.1 to about 500 mg of the composition, e.g., 1, 2, 3, 4, 5, 10, 15, 20, 25, 30, 35, 40, 45, 50, 55, 60, 65, 70, 75, 80, 85, 90, 95, 100, 150, 200, 250, 300, 350, 400, 450, or 500 mg. The unit dose may be administered one or more times daily or intermittently (e.g., once every 2, 3, 4, 5, 6, or 7 days or more) as one or more tablets or capsules each containing from about 0.1 to about 100 mg, conveniently about 0.25 to 50 mg of the composition, e.g., 1, 2, 3, 4, 5, 10, 15, 20, 25, 30, 35, 40, 45, 50, 55, 60, 65, 70, 75, 80, 85, 90, 95, or 100 mg.

In a topical formulation, the composition may be present at a concentration of about 0.01 to 100 mg per gram of carrier. In a preferred embodiment, the composition is present at a concentration of about 0.07-1.0 mg/ml, more preferably, about 0.1-0.5 mg/ml, most preferably, about 0.4 mg/ml.

In addition to administering gossypol acetic acid co-crystals or (−)-gossypol acetic acid co-crystals as a raw chemical, the compositions of the invention may be administered as part of a pharmaceutical preparation containing suitable pharmaceutically acceptable carriers comprising excipients and auxiliaries which facilitate processing of the compositions into preparations which can be used pharmaceutically. Preferably, the preparations, particularly those preparations which can be administered orally or topically and which can be used for the preferred type of administration, such as tablets, dragees, slow release lozenges and capsules, mouth rinses and mouth washes, gels, liquid suspensions, hair rinses, hair gels, shampoos and also preparations which can be administered rectally, such as suppositories, or by aerosol, as well as suitable solutions for administration by injection, topically or orally, contain from about 0.01 to 99 percent, preferably from about 0.25 to 75 percent of active compound(s), together with the excipient.

The pharmaceutical compositions of the invention may be administered to any animal which may experience the beneficial effects of the compounds of the invention. Foremost among such animals are mammals, e.g., humans, although the invention is not intended to be so limited. Other animals include veterinary animals (cows, sheep, pigs, horses, dogs, cats and the like).

The compositions and pharmaceutical compositions thereof may be administered by any means that achieve their intended purpose. For example, administration may be by parenteral, subcutaneous, intravenous, intramuscular, intraperitoneal, transdermal, buccal, intrathecal, intracranial, intranasal, or topical routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Gossypol acetic acid co-crystals or (−)-gossypol acetic acid co-crystals produced by the present methods may exhibit electrostatic properties (e.g., due to triboelectrification) which affect the preparation of dosage forms. Methods known in the art for reducing the affects of electrostatic charges may be used in the preparation of pharmaceutical compositions comprising gossypol acetic acid co-crystals or (−)-gossypol acetic acid co-crystals, e.g., increasing humidity, altering particle size and/or morphology, altering feedstock concentration, avoiding contamination of the surfaces of processing and manufacturing equipment. See, e.g., Rowley, *Int. J. Pharm.* 227:47 (2001); Swaminathan et al., *Drug Dev. Indust. Pharm.* 26:365 (2000); Eilbeck et al., *Int. J. Pharm.* 195:7 (2000); Cassidy et al., *J. Pharm. Pharmacol.* 52:13 (1999); Murtomaa et al., *Eur. J. Pharm. Sci.* 17:195 (2002).

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethyl-cellulose phthalate, are used. Dye stuffs or pigments may be added to the tablets or dragee coatings, for example, for identification or in order to characterize combinations of active compound doses. For tablets comprising gossypol acetic acid co-crystals or (−)-gossypol acetic acid co-crystals, a preferred excipient is silicified microcrystalline cellulose.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

Possible pharmaceutical preparations which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400. Aqueous injection suspensions may contain substances which increase the viscosity of the suspension include, for example, sodium carboxymethyl cellulose, sorbitol, and/or dextran. Optionally, the suspension may also contain stabilizers.

The topical compositions of this invention are formulated preferably as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than $C_{12}$). The preferred carriers are those in which the active ingredient is soluble. Emulsifiers, stabilizers, humectants and antioxidants may also be included as well as agents imparting color or fragrance, if desired. Additionally, transdermal penetration enhancers can be employed in these topical formulations. Examples of such enhancers can be found in U.S. Pat. Nos. 3,989,816 and 4,444,762.

Creams are preferably formulated from a mixture of mineral oil, self-emulsifying beeswax and water in which mixture the active ingredient, dissolved in a small amount of an oil such as almond oil, is admixed. A typical example of such a cream is one which includes about 40 parts water, about 20 parts beeswax, about 40 parts mineral oil and about 1 part almond oil.

Ointments may be formulated by mixing a suspension of the active ingredient in a vegetable oil such as almond oil with warm soft paraffin and allowing the mixture to cool. A typical example of such an ointment is one which includes about 30% almond oil and about 70% white soft paraffin by weight.

Lotions may be conveniently prepared by preparing a suspension of the active ingredient in a suitable high molecular weight alcohol such as propylene glycol or polyethylene glycol.

The following examples are illustrative, but not limiting, of the method and compositions of the present invention. Other suitable modifications and adaptations of the variety of conditions and parameters normally encountered in clinical therapy and which are obvious to those skilled in the art are within the spirit and scope of the invention.

EXAMPLE 1

Production of Gossypol Acetic Acid Co-Crystals

Gossypol acetic acid starting material comprising a mixture of (+)- and (−)-gossypol (100 g) was dissolved in acetone (800 mL) and acetic acid (300 mL) was gradually added. The mixture was allowed to rest at ambient temperature for about one hour and the crystals harvested by vacuum filtration. The crystals were rinsed with 90:10 heptane:acetone (100 mL) followed by heptane (200 mL). The crystals were placed in an amber glass bottle and dried in a vacuum chamber for 1-3 hours.

The gossypol acetic acid co-crystals were recrystallized one to four more times until the desired specifications were met. The co-crystals were dissolved in acetone (8 mL/g co-crystals) with stirring, then acetic acid (3 mL/g co-crystals) was gradually added. The mixture was allowed to rest at ambient temperature for about one hour and the crystals harvested by vacuum filtration. The crystals were rinsed with 90:10 heptane:acetone (10-100 mL) followed by heptane (20-200 mL). The crystals were placed in an amber glass bottle and dried in a vacuum chamber for 1-3 hours.

After each crystallization the co-crystals were assayed by HPLC for chemical purity, chiral purity and by gas chromatography (GC) for residual solvents (acetone, acetic acid, ethyl acetate, heptane).

Additionally, after each recrystallization, the mother liquor was collected by rinsing the filtration apparatus with acetone, adding it to the mother liquor, and drying the mother liquor in a rotary evaporator. The mother liquor solids were assayed by HPLC for chemical purity, chiral purity and by GC residual solvents (acetone, acetic acid, ethyl acetate, heptane). The mother liquor solids were stored at −20 to −10° C. and recrystallized as described above.

EXAMPLE 2

Production of (−)-Gossypol Acetic Acid Co-Crystals

Procedure A. Derivatization Step. Gossypol acetic acid starting material comprising a mixture of (+)- and (−)-gossypol (800 g) was introduced to a reaction flask previously purged with nitrogen. L-phenylalanine methyl ester (758 g) was added, along with dichloromethane (25 Kg) and isopropanol (800 mL) and the mixture was stirred for 1.5 h at ambient temperature. Molecular Sieves type 3A (250 g) were added along with sodium sulfate (480 g) and sodium bicarbonate (336 g) and the mixture was stirred for at least 24 h at ambient temperature. The reaction was monitored by removing a 0.5 mL sample from the reaction mixture, diluting it with dichloromethane (0.5 mL), spotting the sample on a TLC plate, developing the plate with 30% ethyl acetate/heptane and staining with 12. If the reaction was not complete the pH of the reaction mixture was checked. If the pH was less than 6 sodium bicarbonate (70 g) and sodium sulfate (120 g) was added. If the pH was greater than 6, sodium sulfate (120 g) was added. The reaction mixture was stirred for an additional 24 h and checked for completeness. Once the reaction was compete, the mixture was filtered and the residue was washed with dichloromethane (0.5 L). The filtrate was then evaporated in a rotary evaporator set at 35° C. and the residue stored at 2-8° C.

Separation Step. The dried residue (40-50 g) was dissolved in dichloromethane (1 L) and filtered through a 0.45 µm membrane. The filtrate was separated by preparative HPLC using a 10 cm column packed with Kromasil Si (100 angstrom pore size, 10 µm particle size). Each fraction was tested by HPLC for chemical purity, and those fractions containing not less than 95% (−)-gossypol-L-methyl-phenylalaninate-bis-imine were pooled. The pooled fractions were introduced to a Büchi Ball by vacuum, dried on a rotary evaporator set at 30° C., and stored at 2-8° C.

The fractions containing less than 95% (−)-gossypol-L-methyl-phenylalaninate-bis-imine were pooled, introduced to a Büchi Ball by vacuum, and dried on a rotary evaporator set at 30° C. The dried residue was dissolved in dichloromethane at a concentration of 50 mg/mL and passed over the Kromasil Si column again. Fractions containing not less than 95% (−)-gossypol-L-methyl-phenylalaninate-bis-imine were pooled, introduced to a Büchi Ball by vacuum, dried on a rotary evaporator set at 30° C., and stored at 2-8° C.

Hydrolysis Step. (−)-Gossypol-L-methyl-phenylalaninate-bis-imine (800 g) was introduced into a reaction flask that has been previously purged with nitrogen. Tetrahydrofuran (12.9 kg) was added with stirring. The reaction mixture was cooled to 10° C. and degassed. 25% aqueous hydrochloric acid (2.9 L) was added while keeping the reaction mixture temperature below 40° C. and the reaction was stirred for at least 15 h. The reaction was monitored by HPLC. Once the reaction was sufficient, 2.7 M NaCl (3.8 L) was added and the aqueous and organic layers were separated. The aqueous layer was back extracted with ethyl acetate (3.0 L) and the organic layers combined. The organic layer was washed with 1.2 M sodium bicarbonate (4.0 L) followed by 2.7 M NaCl (3.8 L) and then dried by rotary evaporation at 35° C. under reduced pressure. The dried material was dissolved in 50% ethyl acetate/heptane (1.0 L) and passed over a 6 inch silica gel column using 50% ethyl acetate/heptane as the mobile phase. Fractions were monitored by TLC using 80% ethyl acetate/heptane and visualized with UV light. Fractions containing (−)-gossypol were pooled and dried in a rotary evaporator at 35° C. under high vacuum. The dried material was stored at 2-8° C.

Purification of (−) Gossypol over a Diol Column. If the (−)-gossypol was not of sufficient purity at this stage it was further purified over a diol column. (−)-Gossypol (40-50 g) was dissolved in ethyl acetate (10 mL/g). Heptane (10 mL/g) was added and the solution was filtered through a 0.45 µm membrane. The filtrate was separated by preparative HPLC using a 10 cm column packed with YMC Diol (120 angstrom pore size, 10-20 µm particle size; GL Sciences). Each fraction was tested by HPLC for chemical purity, and those fractions containing not less than about 90% (−)-gossypol were pooled. The pooled fractions were introduced to a Büchi Ball by vacuum, dried on a rotary evaporator set at 30° C., and stored at 2-8° C.

The fractions containing less than about 90% (−)-gossypol were pooled, introduced to a Büchi Ball by vacuum and dried on a rotary evaporator set at 30° C. The dried residue was dissolved in 50% ethyl acetate/heptane at a concentration of 50 mg/mL and passed over the column again. Fractions containing not less than 97% (−)-gossypol were pooled, introduced to a Büchi Ball by vacuum, dried on a rotary evaporator set at 30° C., and stored at 2-8° C.

Crystallization and Acetic Acid Exchange. Purified (−)-gossypol was dissolved in acetone (4 mL/g gossypol) to which was added acetic acid (3 mL/g gossypol). The mixture was loaded into a Büchi Ball and the solvent was slowly removed until a crystal mass appeared. The mixture was held for 30 to 60 min and then filtered. The crystals were washed with the same ratio of acetone and acetic acid. The crystals were then soaked in acetic acid for 30 min and the acid was removed by filtration. The crystals were dried in vacuo for 2 to 4 h. The crystals were stored in amber glass vials with Teflon-lined closures at −10 to −20° C.

Procedure B. Derivatization Step. Gossypol acetic acid starting material comprising a mixture of (+)- and (−)-gossypol (1418 g) was slurried with dichloromethane (ACS reagent grade, 6.0 kg) and then the mixture was added to a 50 L reaction flask previously purged with nitrogen. Additional dichloromethane (ACS reagent grade, 12.55 kg) was then added to the flask. USP purified water (7.1 kg) was added to a 50 L separatory funnel along with L-phenylalanine methyl ester hydrochloride (1360 g). The mixture was agitated for 12 min. Then a pre-mixed solution of USP purified water (3.5 kg) and sodium carbonate monohydrate (870 g) was added to the separatory funnel. After 10 min of agitation, dichloromethane (ACS reagent grade, 10.4 kg) was added to the separatory funnel. The resulting mixture was agitated and then allowed to separate into two layers. The layers were separated and the aqueous layer was washed twice with dichloromethane (ACS reagent grade, 4.1 kg). The organic layers were combined and then sodium sulfate (99+% granular, 1.7 kg) was added. After mixing, the mixture in the separatory funnel was filtered using a table top Buchner funnel. The filter cake was washed with dichloromethane and the organic filtrate was added to the 50 L reaction flask along with sodium sulfate (2.2 kg). The mixture was stirred for 2 h and monitored using HPLC and TLC methods. TLC was performed on plates using a 30% ethyl acetate/heptane mobile phase and staining with $I_2$. After completion of the reaction, the reaction mixture was filtered using a table top Buchner funnel and a dichloromethane (0.6 kg) rinse. The dichloromethane filtrate was concentrated to dryness at 35° C. on a large rotary evaporator and tested for purity. The crude residue (~3148 g) was distributed among several tared bottles by adding 40-50 g of crude residue to each bottle. The bottles were stored at −10 to −20° C. until removed individually for the next step. This procedure minimized degradation of the bis imine derivative.

Separation Step. Sequentially over a period of several days, the contents of each bottle was dissolved in sufficient dichloromethane to produce a 50 g/L solution. The solution was filtered through a 20 micron nylon membrane immediately prior to chromatographic separation. The filtrate was separated by preparative HPLC using a 10 cm DAC column packed with ~1000 g of PrincetonSPHER 10-20 mm/100 angstrom silica stationary phase using a heptane/ethyl acetate gradient profile. Each fraction was tested by HPLC for chemical purity. Those fractions containing not less than 95% R (−)-gossypol-L-methyl-phenylalaninate-bis-imine were pooled. The pooled fractions were introduced into a Büchi Ball by vacuum and immediately dried on a rotary evaporator set at 30° C. The flask for this evaporator was removed after each evaporation and placed in a −10 to −20° C. freezer during prolonged idle periods.

The fractions containing less than 95% R (−)-gossypol-L-methyl-phenylalaninate-bis-imine were pooled, introduced to a Büchi Ball by vacuum, and dried on a rotary evaporator set at 30° C. The out of specification material was reprocessed as described above.

A total of ~930 g of R (−)-gossypol-L-methyl-phenylalaninate-bis-imine of >95% purity was obtained. According to a GC analysis, this material contained solvent levels of ~3.9 wt. % of ethyl acetate and 1.9 wt. % of heptanes. This corresponds to an approximate R (−)-gossypol-L-methyl-phenylalaninate-bis-imine content of 876 g.

Hydrolysis Step. R (−)-Gossypol-L-methyl-phenylalaninate-bis-imine (876 g) was introduced into a reaction flask that has been previously purged with nitrogen. Tetrahydrofuran (2.8 Kg) was added with stirring. To this solution USP purified water (1.6 kg) was added followed by glacial acetic acid (7.2 kg). The resulting solution was heated at 35-45° C. When the temperature reached 36° C., concentrated hydrochloric acid (324 g) was added and the temperature was maintained at 35-45° C. until the reaction was complete (~160 min). Then USP purified water (3.5 kg) was added and the mixture was cooled to ~17° C. overnight. The mixture was filtered using a 12 inch Buchner funnel set up inside a glove bag. The filter cake was rinsed with USP purified water (~3 kg) and then transferred to two 80 oz amber bottles. Each bottle was filled to no more than half full with solids. Enough 6:1 water:acetic acid solution (~5.3 kg water and ~0.89 kg acetic acid) was added to fill each bottle. The contents of each bottle were shaken to form a slurry. The contents of both bottles was added to a 50 L flask that had been purged with nitrogen gas. The remaining portion of the 6:1 water:acetic acid was used as a rinse to aid the transfer. The slurry was stirred for 2 h and 35 min. The slurry was filtered and the filter cake was rinsed with USP purified water (3 kg). The rinsed filter cake was transferred to two 80 oz amber glass bottles. One bottle contained 592 g of crude R (−) gossypol, the other bottle contained 795 g of crude R (−) gossypol.

Crystallization. The contents of the bottle containing 795 g of crude R (−) gossypol was transferred to a Büchi Ball rotary evaporator flask with the aid of some acetone. The contents of the Büchi Ball after drying (800 g) was dissolved in acetone (3200 mL). Turbidity and crystal growth was evident almost immediately upon dissolution. The flask was sealed and the mixture was held at room temperature. After ~50 min of crystal growth the mixture was filtered and the filter cake was rinsed with 9:1 heptane:acetone solution (400 mL) and then with heptane (100 mL). The filter cake (~179 g) was placed in a vacuum chamber and dried for 1 h giving 109 g of dried R (−)-gossypol acetone co-crystals. The mother liquor from the crystallization was evaporated to dryness, dissolved in ethyl acetate and washed with brine in a separatory funnel. The organic layer was collected, evaporated to dryness (270 g) and crystallized as above to obtain a second batch (119 g) of R (−) gossypol acetone co-crystals. A third batch obtained similarly did not meet specifications. The solids obtained from the third batch were dissolved in ethyl acetate and washed with brine. The organic layer was concentrated to dryness (58 g) and crystallized from acetone as described above affording 13 g of R (−) gossypol that was within specifications.

Acetic Acid Exchange. A 238-g sample of R (−) gossypol acetone co-crystals that were within specifications was added to a crystallization dish. To the dish was added acetic acid (900 mL) and the slurry was held at room temperature for 14 min. The slurry was filtered, rinsed with acetic acid (100 mL) and transferred to a drying tray. The damp filter cake was spread out evenly to maximize exposed surface area. The drying tray was sealed in a drying bag and placed in a vacuum chamber at room temperature. The material was dried (~168 h) to constant weight (160 g) and packaged in a 500 mL wide mouth, amber glass bottle.

Alternate Procedure for Preparing the L-methyl-phenylalaninate-bis-imine from Gossypol. A mechanically stirred slurry of gossypol acetic acid starting material comprising a mixture of (+)- and (−)-gossypol (50.0 g; 86.4 mmol) and L-phenylalanine methyl ester hydrochloride (41.4 g; 192.0 mmol) in dichloromethane (1000 mL) was treated with neat triethylamine (27.6 mL; 198.0 mmol) in one portion to give a homogenous solution within several minutes. The dark brown solution was stirred under nitrogen at ambient temperature. After 5 h, an aliquot (2 drops) was taken and stripped on a rotary evaporator and then diluted with 15 mL acetonitrile. HPLC analysis showed a 1:1 mix of the diastereomers (97.5 area %) with 2 minor impurities. After 6 h, the brown solution was poured into deionized water (750 mL) at ambient temperature. The flask was rinsed with dichloromethane (15 mL) and added to the two phase mixture. The two phases were vigorously mixed and allowed to settle for 10 min. The brown dichloromethane layer was separated and concentrated on a rotary evaporator at 20-30° C. with a Büchi pump to give a golden brown solid (94.8 g). This solid was evacuated at high vacuum (0.25 torr) and ambient temperature overnight. After 14.5 h of evacuation, the amount of yellow-gold solid was 72.1 g (99.2% yield). HPLC analysis showed the two diastereomers in about 97% purity (AUC) with the 3 minor impurities and some residual L-phenylalanine methyl ester. Proton NMR analysis showed the desired diastereomers in high purity (98 wt %) with some residual dichloromethane (1.8 wt %) and acetic acid (0.3 wt %).

EXAMPLE 3

Pharmaceutical Formulations

Gossypol acetic acid co-crystals or (−)-gossypol acetic acid co-crystals may be formulated as tablets as shown in Table 2.

TABLE 2

| Ingredient | Amount | |
| --- | --- | --- |
| Gossypol acetic acid co-crystals | | 10.0 mg |
| (−)-Gossypol acetic acid co-crystals | 5.0 mg | |
| Silicified microcrystalline cellulose | 166.0 mg | 161.0 mg |
| Sodium starch glycolate | 4.5 mg | 4.5 mg |
| Stearic acid | 4.5 mg | 4.5 mg |

Having now fully described the invention, it will be understood by those of skill in the art that the same can be performed within a wide and equivalent range of conditions, formulations, and other parameters without affecting the scope of the invention or any embodiment thereof. All patents, patent applications and publications cited herein are fully incorporated by reference herein in their entirety.

What is claimed is:

1. A method of producing (−)-gossypol acetic acid co-crystals from (−)-gossypol acetone co-crystals, comprising substituting the acetone in said (−)-gossypol acetone co-crystals with acetic acid to form (−)-gossypol acetic acid co-crystals.

2. The method of claim 1 consisting essentially of adding acetic acid to said (−)-gossypol acetone co-crystals to produce a slurry, filtering said slurry, rinsing the solid thus obtained with acetic acid, and drying said solid to give said (−)-gossypol acetic acid co-crystals.

* * * * *